United States Patent
Puleo et al.

(10) Patent No.: US 9,895,354 B2
(45) Date of Patent: Feb. 20, 2018

(54) BILAYERED CALCIUM SULFATE/CALCIUM PHOSPHATE SPACE-MAKING COMPOSITES WITH MULTIPLE DRUG DELIVERY CAPABILITIES

(71) Applicant: University of Kentucky Research Foundation, Lexington, KY (US)

(72) Inventors: David Puleo, Lexington, KY (US); Bryan Orellana, Lexington, KY (US); Mike McQuinn, Lexington, KY (US)

(73) Assignee: UNIVERSITY OF KENTUCKY RESEARCH FOUNDATION, Lexington, KY (US)

( * ) Notice: Subject to any disclaimer, the term of this patent is extended or adjusted under 35 U.S.C. 154(b) by 0 days.

(21) Appl. No.: 14/678,457

(22) Filed: Apr. 3, 2015

(65) Prior Publication Data

US 2015/0283089 A1 Oct. 8, 2015

Related U.S. Application Data

(60) Provisional application No. 61/975,133, filed on Apr. 4, 2014.

(51) Int. Cl.
| | |
|---|---|
| *A61K 9/14* | (2006.01) |
| *A61K 31/4174* | (2006.01) |
| *A61K 31/366* | (2006.01) |
| *A61L 27/54* | (2006.01) |
| *A61K 9/20* | (2006.01) |
| *A61K 9/24* | (2006.01) |
| *A61L 27/46* | (2006.01) |
| *A61L 27/52* | (2006.01) |
| *A61K 31/4164* | (2006.01) |

(52) U.S. Cl.
CPC .......... *A61K 31/4174* (2013.01); *A61K 9/146* (2013.01); *A61K 9/209* (2013.01); *A61K 9/2009* (2013.01); *A61K 9/2086* (2013.01); *A61K 9/2095* (2013.01); *A61K 31/366* (2013.01); *A61K 31/4164* (2013.01); *A61L 27/46* (2013.01); *A61L 27/52* (2013.01); *A61L 27/54* (2013.01)

(58) Field of Classification Search
CPC .. A61K 9/5015; A61K 9/145; A61K 31/4174; A61K 31/366
USPC .......... 424/484, 497; 514/398, 460
See application file for complete search history.

(56) References Cited

U.S. PATENT DOCUMENTS

| | | | |
|---|---|---|---|
| 5,462,722 A | 10/1995 | Liu et al. | |
| 5,776,193 A | 7/1998 | Kwan et al. | |
| 6,030,636 A | 2/2000 | Randolph et al. | |
| 6,311,690 B1 | 11/2001 | Jefferies | |
| 6,764,517 B2 | 7/2004 | Yamamoto et al. | |
| 6,998,137 B2 | 2/2006 | Shih et al. | |
| 7,241,316 B2 | 7/2007 | Evans et al. | |
| 7,575,780 B2 | 8/2009 | Alexander et al. | |
| 7,758,882 B2 | 7/2010 | Roeder et al. | |
| 7,833,278 B2 | 11/2010 | Evans et al. | |
| 7,863,352 B2 | 1/2011 | Ricci et al. | |
| 7,892,291 B2 | 2/2011 | Evans et al. | |
| 8,012,501 B2 | 9/2011 | Kerr et al. | |
| 8,419,802 B2 | 4/2013 | Evans et al. | |
| 8,496,955 B2 | 7/2013 | Cooper | |
| 8,586,074 B2 | 11/2013 | Mamidwar et al. | |
| 8,603,183 B2 | 12/2013 | Ding | |
| 2003/0045924 A1* | 3/2003 | Datta | A61F 2/88 623/1.15 |
| 2004/0002770 A1 | 1/2004 | King et al. | |
| 2007/0190102 A1 | 8/2007 | Luo | |
| 2007/0248675 A1 | 10/2007 | Tae et al. | |
| 2007/0255422 A1 | 11/2007 | Wei et al. | |
| 2008/0233165 A1 | 9/2008 | Alexander et al. | |
| 2008/0292839 A1* | 11/2008 | Wei | A61L 27/46 428/113 |
| 2010/0185200 A1 | 7/2010 | Dricot | |
| 2011/0060413 A1 | 3/2011 | Kasuga et al. | |
| 2011/0208305 A1 | 8/2011 | Malinin et al. | |
| 2012/0053692 A1 | 3/2012 | Voor et al. | |
| 2012/0095518 A1 | 4/2012 | Ju et al. | |
| 2012/0136441 A1 | 5/2012 | Yang et al. | |
| 2012/0189683 A1 | 7/2012 | Yang et al. | |
| 2012/0207839 A1 | 8/2012 | Liu et al. | |
| 2012/0310366 A1* | 12/2012 | Li | A61K 31/22 623/23.57 |
| 2013/0171221 A1 | 7/2013 | Deng et al. | |
| 2013/0273135 A1 | 10/2013 | Brooks et al. | |
| 2013/0297038 A1* | 11/2013 | McKay | A61F 2/28 623/23.57 |
| 2013/0345825 A1 | 12/2013 | Bufler | |

OTHER PUBLICATIONS

Chou et al.; Title: Controlled Release of Simvastatin from Biomimetic β-TCP Drug Delivery System; PLOS ONE. Jan. 2013, vol. 8 Issue 1, Special section p. 1-6.*
Greenwald et al, title: Bone-graft substitutes: facts, fictions & applications, American academy of orthopedic surgeons, 73rd Annual Meeting, Mar. 22-26, 2006.*
Author: Orellana et al.; Title: Bioerodible calcium sulfate/poly((β-amino ester) hydrogel composites, J Mech Behav Biomed Mater. Oct. 2013;26:43-53; Epub May 31, 2013.*

* cited by examiner

Primary Examiner — Yanzhi Zhang
(74) Attorney, Agent, or Firm — King & Schickli PLLC

(57) ABSTRACT

The present invention provides for bilayered composites that provide for sustained drug delivery and support to recovering tissue(s) and areas surrounding, such as with bone tissue. The two layers degrade at separate rates, thereby providing sustained mechanical support and tailored drug delivery.

20 Claims, 19 Drawing Sheets

A.

B.

A.

B.

A

B

BILAYERED CALCIUM SULFATE/CALCIUM PHOSPHATE SPACE-MAKING COMPOSITES WITH MULTIPLE DRUG DELIVERY CAPABILITIES

RELATED APPLICATIONS

This application claims priority to U.S. Provisional Patent Application 61/975,133, filed 4 Apr. 2014, which is hereby incorporated by reference in its entirety.

GOVERNMENT INTEREST

This invention was made with Government support from grants NIH DE019645 and EPS-0814194 awarded by the National Institutes for Health and the National Science Foundation, respectively. The Government may have certain rights in the invention.

TECHNICAL FIELD

The present invention relates generally to methods of improving bone regeneration or augmentation through the introduction of bilayered composites comprising an outer shell and an inner core, wherein the two layers degrade or erode at different rates in situ, thereby allowing for mechanical support to tissues while improving administration of therapeutic compounds dispersed within one or both of the layers.

BACKGROUND

A traumatic event to the bone, such as that seen with surgical procedures, can require many varied therapies to improve recovery and healing. Often it is contemplated that providing mechanical support in conjunction with delivering therapeutic compounds at the surgical site can aid in improving the recovery process. However, the differing rates of absorption and metabolism can make effective delivery very complicated. The capacity to quickly regenerate or augment bone lost as a result of resorption and trauma is crucial to restoring proper function and aesthetics. In addition to existing bone grafts, both autologous and allogeneic, a variety of bone graft substitutes are being developed (Ilan D. I, Ladd A. L. (2004) Bone graft substitutes, *Operative Techniques in Plastic and Reconstructive Surgery*, 9.4, 151-160).

A common procedure to treat osseous defects is bone grafting which takes tissue from a donor site that is transplanted to a defective region. For instance, in dentistry, this procedure is used in conjugation with guided bone regeneration (GBR) for regions in the mandible where bone has been resorbed or deformed due to the loss of teeth, periodontal disease or trauma to the jaw. GBR is a procedure which implants a barrier membrane over donated bone material to prevent infiltration of epithelium and connective tissue which may disrupt bone formation (Simion, M., Fontana, F., Rasperini, G., Maiorana, C., 2007. Vertical ridge augmentation by expanded-polytetrafluoroethylene membrane and a combination of intraoral autogenous bonegraft and deproteinized anorganic bovine bone (Bio Oss). Clinical Oral Implants Research 18, 620-629). Depending on the barrier material, there can be a tendency to collapse, which will require bone grafting to provide a biodegradable and stable support structure as osteogenesis occurs (Hitti, R. A., Kerns, D. G., 2011. Guided bone regeneration in the oral cavity: a review. Open Pathology Journal 5, 33-45). However, these procedures also may require a second surgery to remove non-biodegradable barrier membranes, and bone grafting may cause morbidity in the donor site (Chiapasco, M., Zaniboni, M., Rimondini, L., 2007. Autogenous onlay bone grafts vs. alveolar distraction osteogenesis for the correction of vertically deficient edentulous ridges: a 2-4-year prospective study on humans. Clinical Oral Implants Research 18, 432-440; Guarnieri, R., Grassi, R., Ripari, M., Pecora, G., 2006. Maxillary sinus augmentation using granular calcium sulfate (surgiplaster sinus): radiographic and histologic study at 2 years. International Journal of Periodontics and Restorative Dentistry 26, 79-85; Triplett, R. G., Schow, S. R., 1996. Autologous bone grafts and endosseous implants: Complementary techniques. Journal of Oral and Maxillofacial Surgery 54, 486-494). A strong biocompatible material that can effectively promote osteogenesis while acting as an effective barrier and/or support thus preventing disruptive tissue from infiltrating would be an effective alternative for the procedure. Release of bioactive agents and/or the combination of materials to create a stable augmenting platform could be a suitable substitute to the existing standard autografts.

SUMMARY OF THE INVENTION

The present invention provides for a bilayered composite to provide mechanical support, as well as to provide localized drug delivery comprising an outer shell layer and an inner core layer, wherein one layer degrades in situ within a subject at a rate faster than the other layer. The outer shell layer may degrade faster than the inner core layer, or the inner core layer may degrade faster than the outer shell layer.

One layer may comprise a material selected from the group consisting of dicalcium phosphate dihydrate (DCPD), hydroxyapatite, calcium-deficient hydroxyapatite, carbonate-substituted hydroxyapatite, and calcium polyphosphate. The other layer may comprise a material selected from the group consisting of calcium sulfate (CS), (3-tricalcium phosphate, amorphous calcium phosphate, monetite, and tetracalcium phosphate.

In certain embodiments, one layer comprises calcium sulfate and the other layer comprises calcium phosphate. The calcium phosphate may be dicalcium phosphate dehydrate.

In certain embodiments, at least one layer further may comprise a pharmaceutical agent selected from the group consisting of: simvastatin, lovastatin, rosuvastatin, SVAK-12, bone morphogenetic proteins, parathyroid hormone (1-34), metronidazole, doxycycline, vancomycin, gentamycin, ciprofloxacin, ketoprofen, celecoxib, diclofenac, meloxicam or combinations thereof. In other embodiments, both layers further comprise a pharmaceutical agent. Optionally, the pharmaceutical agent may be preloaded in a degradable matrix or a hydrogel.

The present invention also provides methods of providing tissue support to a subject in need thereof, comprising administering the bilayered composite to tissue of a subject. The tissue may be osseous tissue. The subject may be an animal, such as a vertebrate. The subject may be a fish, mammal, amphibian, reptile or bird. The subject may be a human. The methods may further comprise preloading at least one layer with a pharmaceutical agent. Optionally, the pharmaceutical agent is in a degradable matrix or hydrogel within the layer.

DESCRIPTION

Figure 1:
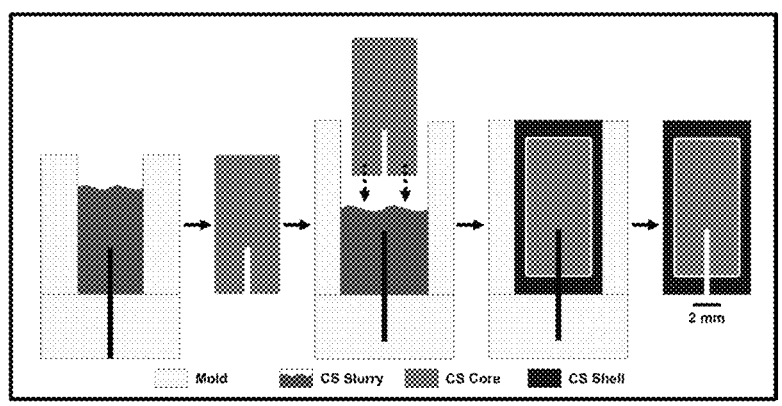
FIG. 1 shows a schematic depicting the process of forming a bilayered CS composite. From left to right: core formation; insertion of core into shell mold; final composite showing core encased within a CS shell. Images are to scale.

The present invention provides for a bilayered composite to assist in bone augmentation, such as rebuilding and healing at the site of injury or surgical repair to bone or osseous tissue, such as that seen with dental or orthopedic surgeries. The bilayered composites of the present invention comprise an outer shell layer and an inner core layer. Either layer may be loaded or incorporated with a therapeutic compound, either both with the same or with different compounds. The two layers are comprised of biomaterials that degrade or erode at different rates once placed in situ within a subject. The bilayered composites, in addition to delivering therapeutic compounds, further provide structural protection, such as a "tenting" of surrounding soft tissue to create a regeneration chamber for bone, thus removing need for harvesting tissue for grafts. The following describe background of the present invention: Oreliana, B. R., Thomas, M. V., Hilt, J. Z., and Puleo, D. A. (2013). Bioerodible calcium sulfate hemihydrate/poly(β-amino ester) hydrogel composites, J. Mech. Behav. Biomed. Mater. 26:43-53; Oreliana, B. R. and Puleo, D. A. (2014). Tailored sequential drug release from bilayered calcium sulfate composites, Mater Sci Eng C Mater Biol Appl. 43:243-52; Oreliana, B. R., Hilt, J. Z., and Puleo, D. A. (2015). Drug release from calcium sulfate-based composites, J. Biomed Mater Res. Part B 2015 103(1):135-42; Oreliana, B., Hawkins, A. M., Thomas, M. V., Hilt, J. Z., and Puleo, D. A. (2010). Calcium sulfate/hydrogel space-making composites for bone augmentation. Presented at the 2010 Annual Meeting of the Society For Biomaterials, April 21-24, Seattle, Wash.; Oreliana, B. R, Thomas, M. V., Hilt, J. Z., and Puleo, D. A. (2011). Drug delivery from calcium sulfate/hydrogel space-making composites. Presented at the 2011 Annual Meeting of the Society For Biomaterials, April 13-16, Orlando, Fla.; Oreliana, B. R., Thomas, M. V., Hilt, J. Z., and Puleo, D. A. (2012). Drug delivery from space-Making calcium sulfate/poly(β-amino ester) hydrogel composites. Presented at the AADR Annual Meeting, March 21-24, Tampa, Fla.; Oreliana, B. R., Thomas, M. V., Hilt, J. Z., and Puleo, D. A. (2013). Bilayered calcium sulfate space-making composites with multiple drug delivery capabilities. Presented at the 2013 Annual Meeting of the Society For Biomaterials, April 10-13, Boston, Mass.; Oreliana, B. R., McQuinn, M. W., and Puleo, D. A. (2014). Tailored properties of bilayered calcium sulfate and calcium phosphate bone graft substitutes. Presented at the 2014 Annual Meeting of the Society For Biomaterials, April 16-19, Denver, Colo.; McQuinn, M. W., Oreliana, B. R., and Puleo, D. A. (2014). Bilayered calcium phosphate/calcium sulfate bone graft substitutes. Presented at the 2014 Annual Meeting of the American Association of Oral and Maxillofacial Surgeons, September 8-13, Honolulu, Hi.; Gu, Y., Oreliana, B. R., and Puleo, D. A. (2015). Simvastatin-releasing calcium sulfate and calcium phosphate bioceramics. Presented at the 2015 Annual Meeting of the Society For Biomaterials, April 15-18, Charlotte, N.C.

Because space maintenance and stimulation of osteogenesis is important for many dental, craniofacial, and orthopedic procedures, the implanted bilayered composites of the present invention can be useful in many applications requiring bone grafting/bone graft substitutes. These include ridge augmentation for placement of dental implants, ridge preservation following tooth extraction, reconstruction of cavitary bone defects, regeneration in segmental bone loss, and enhancement of interbody spinal fusion.

The bilayered composite system of the present invention is amenable to formulation with varied biomaterials. According to the present invention, one of the selected biomaterials should be proceed at a slower eroding/degrading/dissolving rate than the other. Those skilled in the art will appreciate that different benefits may be achieved when the order of the layers is varied. For example, placement of the more rapid degrading biomaterial as the outer shell, allows for faster rates of therapeutic delivery of compounds contained in the outer layer, as well as a faster access to the slower degrading core and any therapeutic compounds contained therein. Conversely, placement of the slower degrading biomaterial as the outer core allows for reduced rates of release of therapeutic compounds from this layer, as well as a prolonged time of access to the core, as well as any therapeutics contained therein.

As set forth in the working examples, dicalcium phosphate dihydrate (DCPD or brushite, a form of calcium phosphate, CP) provides for a slower degrading biomaterial and calcium sulfate (CS) is a faster degrading biomaterial. Other possible biomaterials include, but are not limited, to the following:
  Slower degrading: hydroxyapatite, calcium-deficient hydroxyapatite, carbonate-substituted hydroxyapatite, and calcium polyphosphate
  Faster degrading: β-tricalcium phosphate, amorphous calcium phosphate, monetite, and tetracalcium phosphate Further, as set forth in the working examples, metronidazole and simvastatin can be used as antimicrobial and osteogenic agents that are impregnated or deposited into the layers of the bilayered composite. Those skilled in the art will appreciate that any therapeutic compound can be considered, taking into account the respective solvency once in situ, as well as how a selected agent may align/interact with a potential biomaterial that formulates the particular layer. Particular classes of therapeutic compound are worth considering given the purpose of assisting in bone augmentation. These include, but are not limited, to the following:
  Antimicrobial agents—such as: metronidazole, doxycycline, vancomycin, gentamycin, and ciprofloxacin
  Osteogenic agents—such as: simvastatin, lovastatin, rosuvastatin, SVAK-12, bone morphogenetic proteins, and parathyroid hormone (1-34)
  Anti-inflammatory agents—such as: ketoprofen, celecoxib, diclofenac, and meloxicam Those skilled in the art will appreciate that the therapeutic agents incorporated within each layer may be further incased in an additional biomaterial, such as a hydrogel or degradable matrix, to further affect the release. Examples include, but are not limited to poly (lactic-co-glycolic) acid (PLGA), poly(β-amino ester) (PBAE), cellulose acetate phthalate and phronic F-127.

The tailorable bilayered composites may function as bone graft substitutes or part thereof and provide the ability once in situ to sequentially release multiple therapeutic agents. As set forth in the working examples herein, microcomputed tomography (MicroCT) images exemplify the overall layered geometry as well as uniform distribution of particles within the bilayered composites.

Those skilled in the art will appreciate that the portion each layer contributes to the overall composition can alter the activity and function when in situ. For example, the working examples provide a demonstration of release of simvastatin within a CS layer. The data generated from sustained release of simvastatin directly loaded into CS demonstrate that changing the shell to core volume ratio dictates the duration of drug release from each layer.

By introducing a tunable layered geometry capable of releasing multiple drugs, the bilayered composites of the present invention provide bone graft substitutes that can be tailored in order to help streamline multiple steps needed to regenerate tissue in infected defects. As also demonstrated in the working examples, when loaded together in the shell or in separate layers, sequential release of two therapeutic agents is achieved. Qualitative assessment of the morphology of bilayered composites showed good distribution of therapeutic carrying degradable matrix, such as PLGA, microparticles (without or loaded with a therapeutic agent) embedded in at least one layer of the bilayer composite between 1 and 10 wt %. Those skilled in the art will appreciate that higher content can also be utilized, particularly in instances where the mechanical support is of reduced concern, such as with non-load bearing sites. Although the embedded particles were distributed throughout the matrix, they did not appear to be interconnected, which otherwise would have allowed for fluid to seep into the composite. During erosion, closed pockets with drug-loaded particles near the surface were exposed, thereby releasing the polymer particles. The introduction of a bilayered geometry affected properties compared to solid samples, with a reduction in the strength and elastic modulus. The loading of therapeutic compounds directly into the shell, core, or both layers did not significantly affect the strength of the bilayered composites. The layered geometry used from the examples described herein demonstrate a unique platform for achieving customizable sequential release of therapeutic agents. Loading of drug carrying microparticles into the matrix allows for further tailoring of drug release.

The release of therapeutic compounds and the carriers thereof can be tailored depending on the layer in which the therapeutics are loaded. For example, as set forth in the examples, simvastatin delivery can be tailored depending on whether it was the shell only, core only, or both.

To further adjust the duration or even the delay of drug release from either the shell or core, the shell to core volume ratio can be altered. For example, the findings for samples with metronidazole within PLGA particles and with simvastatin directly loaded into a shell demonstrated sequential release: polymeric particles loaded with metronidazole and embedded into the shell were exposed as the shell experienced surface erosion, and a sustained release of the drug occurred as the PLGA particles subsequently degraded. To further enhance the process of fighting infection and then regenerating lost tissue, release of an anti-bacterial agent from the graft starting at the time of implantation can be beneficial to help reduce the overall healing time. The release of a therapeutic, as seen with simvastatin in the examples, is, therefore, governed by the surface erosion characteristics, which have demonstrated to be linear, allowing for a near constant rate of release of simvastatin. The apparent differences in release kinetics between the two drugs and their means of loading allowed for enough separation for all the metronidazole to be released approximately 4 days sooner than simvastatin. Conversely, when simvastatin was loaded into only the core and PLGA particles loaded with metronidazole remained in the shell, there was a much greater lapse in time for a fully separated sequential release to occur. Instances such as this can mimic the clinical sequence of events for treating infection and subsequently restoring lost or damaged tissue. When metronidazole and simvastatin were loaded together in the shell or in separate layers, temporal separation of the two drugs was achieved.

The ability of the present invention to provide tailored release of therapeutic agents as well as a sequential release of different drugs, may be utilized in many scenarios, such as a bone graft substitute for treating infected bony defects, e.g., periodontal pockets. Changing the shell to core volume ratio dictates the duration of drug release from each layer.

With the bilayered composites of the present invention, the ratio of shell to core may vary according to the desired outcome. The percent of shell to the total composite may be 5, 10, 15, 20, 25, 30, 35, 40, 45, 50, 55, 60, 65, 70, 75, 80, 85, 90, or 95%. Conversely, the percent of the core to the total composite may be 5, 10, 15, 20, 25, 30, 35, 40, 45, 50, 55, 60, 65, 70, 75, 80, 85, 90, or 95%.

The therapeutic compounds loaded into the layers of the composite may comprise any known pharmacologic agent or any combination thereof. Therapeutic agents may be encased or protected prior to loading within either layer of the shell, such as with degradable matrices like PLGA. Examples of therapeutic compounds that may be beneficial to osseous tissue, such as bone and/or dental areas, receiving the bilayered composites include: proteins/growth factors, such as bone morphogenetic proteins (BMPs) 2, 4, 7, and 9; statin drugs, such as simvastatin, lovastatin, fluvastatin, and mevastatin; antibiotics, such as metronidazole, doxycycline, gentamicin, and vancomycin; and anti-inflammatory agents, such as ketoprofen, naproxen, and celecoxib.

With regard to oral surgeries, in testing the bilayered composites, it was noted that although the compressive properties decreased with the introduction of a layered geometry, the resulting strengths seen with faster degrading materials, such as calcium sulfate, in the bilayered composites remained either similar to or stronger than the strength of trabecular bone in the mandible and the combination of the faster/slower degrading materials, such as calcium sulfate/calcium phosphate samples, were even stronger still.

Figure 8:
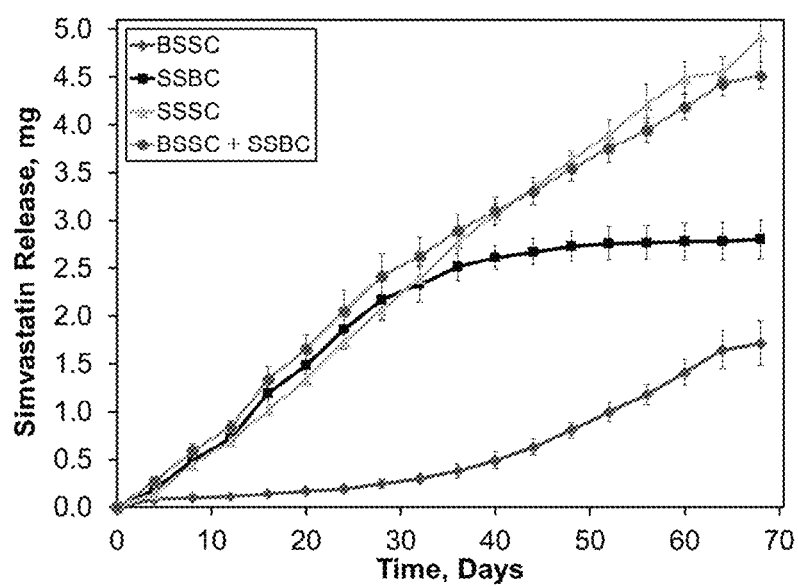
FIG. 8 shows cumulative release of simvastatin from bilayered samples incubated below sink conditions. The samples tested had a 50:50 shell to core volume ratio. Data are mean±standard deviation (n=5).

The present invention provides for bilayered composites in a variety of final shapes. Preformed scaffolds can be designed to allow fabrication of a variety of shapes. The bilayered geometry allows for sequential release of multiple drugs. Incorporated biomaterial of differing degradation rates, such as CS and DCPD, into separate layers allows for customizable erosion. For example, structures can exhibit fast initial erosion of a CS shell while maintaining the DCPD core and vice versa. Examples of microCT reconstructions of dissolution trends are seen in FIG. 8.

The erosion pattern of the layered materials within the bilayered composites allows for erosion tuning and customizable drug release that further assist in functioning as a bone graft substitute. Slower degrading biomaterials, such as DCPD, have demonstrated to be a more durable ceramic as compared to fast degrading materials, such as CS, lasting well over 180 days in release studies. For example, DCPD samples sustained much larger compressive forces and released at much slower yet steady rates in lower loadings. The bulk degradation property of CP may be beneficial for bone augmentation by allowing for cell infiltration and increasing surface area for growth. Bilayered composites are able to degrade and permit more space for bone growth than non-layered samples of slower degrading material, such as DCPD, while also maintaining a longer lasting support structure, unlike faster degrading materials like CS.

Bilayered composites of the present invention can further act as 'tenting' barriers to prevent or hinder soft tissue infiltration, while allowing a well-tailored delivery of a variety of treatment specific drugs directly loaded in the material of a particular layer and/or embedded in biodegradable hydrogel particles. The release of bioactive agents and/or the combination of materials to create a stable augmenting platform suitable as a substitute to the existing standard autografts.

Figure 15:
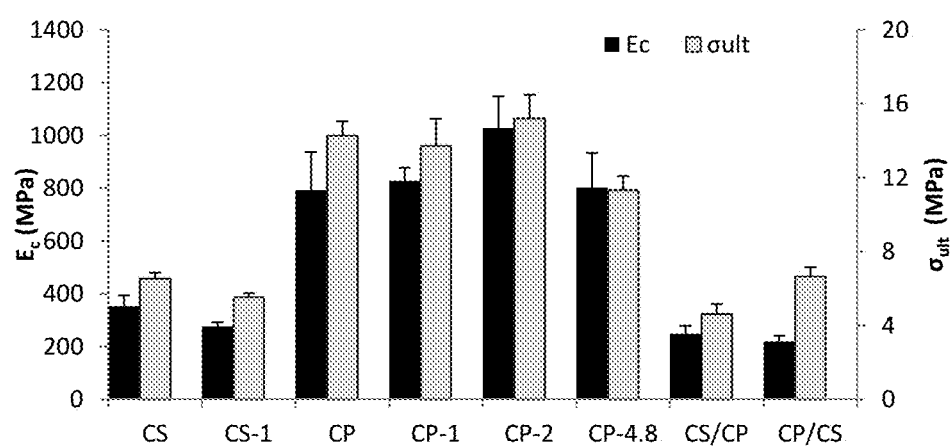
FIG. 15 shows compressive elastic modulus and ultimate compressive stress of non-layered and bilayered CS and DCPD implants at different simvastatin loadings in non-layered samples. Data is mean±SEM (n=8-10).
Figure 17:
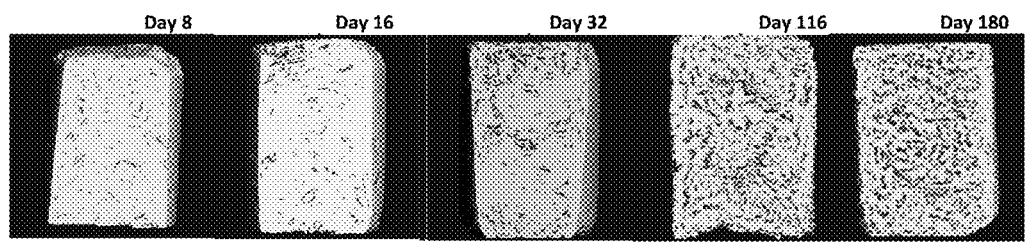
FIG. 17 shows microCT cross-sections of DCPD samples during erosion in PBS.

The bilayered composites of the present invention provide for a composite that retains the benefits from the properties of the biomaterial of each layer, with the addition of the other layer overcoming any deficiencies. For example, as set forth in the working examples, release of simvastatin directly loaded into a "fast" degrading material implant, calcium sulfate (CS), and a "slow" degrading material implant, calcium phosphate (CP) (such as DCPD), demonstrated release rates of approximately 59 and 7 µg/day for CS and CP, respectively. Mechanical testing showed CP to have significantly ($p<0.05$) greater compressive strength (FIG. 15 and modulus than did CS. There were no significant differences between CP of different simvastatin loadings. CP eroded much more slowly than CS when incubated in phosphate-buffered saline; CS was gone within 28 days, while CP lasted more than 180 days. Loading did not affect erosion. MicroCT scans showed that CP developed a porous internal structure as it eroded (FIG. 17). However, in combining the slow dissolving properties of DCPD with CS in a bilayered composite, a 'middle ground' is established where sufficient scaffolding is maintained as CS dissolves and cell infiltration occurs in the slower dissolving DCPD. Release of simvastatin from CS samples occurred at a much higher rate than DCPD samples, as expected from CS's faster dissolution rate. Release rates were approximately 247 and 29 µg/day for CS-1 and CP-1, respectively. Increasing the amount of simvastatin added to DCPD resulted in a loading-dependent increase in release rate (i.e., 45 and 105 µg/day for 2 and 4.8 wt % simvastain loadings, respectively). Mechanical testing showed DCPD to all have significantly ($p<0.05$) greater ultimate compressive strength and compressive modulus than did CS (FIG. 15). Additionally the strength and modulus of both bilayered samples were significantly lower ($p<0.01$) than that of DCPD blanks. The compressive mechanical properties of both bilayered samples were comparable ($p>0.05$) to that of CS blanks. There was also no significant difference found between the compressive mechanical properties of CS/CP bilayering compared to CP/CS bilayering. MicroCT scans also showed qualitatively that DCPD developed a porous internal structure as it eroded.

According to the present invention, higher loadings should be preferred over lower loadings in order to achieve a higher average release rate, while lower loadings are preferred over higher loadings in order to achieve a steadier release rate. Due to rapid dissolution, faster degrading material as the shell layering has a higher release rate in the first weeks of its dissolution. Additionally, such samples result in greater mass loss since more surface area is exposed, leaving behind the slower degrading core. This is beneficial for providing longer-lasting scaffolding for implantations while also allowing room for sufficient bone growth as the outer shell layer dissolves.

Degradation of the implants can be slowed by selecting a slower degrading material as an outer shell and selecting the faster degrading material to compromise the inner core. As described herein, with the slower degrading DCPD and faster degrading CS, DCPDs/CS and CS/DCPDs formulations had a slower yet more linear release rate compared to other bilayered formulations. DCPD shells release at a higher rate by occupying more volume compared to DCPD cores. The formation of an empty core as slow degrading-shell samples dissolve can also be beneficial for providing greater mechanical strength than a using a slow degrading core while also allowing for bone growth to occur at the center of the shell. The quality for both fast and slow degrading materials to retain their mechanical properties at the loadings tested provides for more options in controlled drug release which is important for regions of bone defect where healing is slower and requires increased drug loadings to compensate. The mechanical properties observed in the examples were also found to be higher than those of trabecular bone in the mandibles (96.2 MPa compressive modulus; 3.9 MPa ultimate compressive strength) (Misch C E, Qu Z, Bidez M W. Mechanical properties of trabecular bone in the human mandible: Implications for dental implant treatment planning and surgical placement. J Oral Maxil Surg. 1999; 57:700-6; McQuinn, M. (2014, September). *Bilayered Calcium Phosphate/Calcium Sulfate Bone Graft Substitutes*. Poster presented at the 96$^{th}$ Annual Scientific Sessions & Exhibition, Honolulu, Hi.). Accordingly, while the bilayered composites may not be as stiff as non-layered samples, they can carry the same load before failure. A redeeming quality is that the inclusion of slower degrading materials allows for an adequate support structure in implantation sites much longer due to its slower dissolution. The structure of slower degrading materials, such as DCPD, allows for infiltration of cells such as osteoblasts as it degrades while osteogenic activities can promoted by the local release of a therapeutics (seen with simvastatin in the examples). MicroCT scans of such embodiments showed slight surface imperfections in DCPD samples even before degradation testing began. These surface imperfections were found to be as wide as 100 μm in diameter which is sufficient to permit infiltration of osteoblasts (20-30 μm). The much slower degradation rate is also beneficial for maintaining a slow consistent release over a sustained period time as observed in the release study. These issues can be addressed by combining the two ceramics using the bilayered composites, thereby providing a longer lasting support structure (e.g., DCPD) while also permitting sufficient bone growth to occur within the core as the faster degrading material (e.g., CS) is dissolved. Further, after bone ingrowth has occurred within the core of the slower degrading shell, mechanical properties can expect to see a boost due to the presence of both bone and the shell. Additionally, cell infiltration and resorption can occur on both sides of the shell, thereby allowing for better integration of bone and effectively reducing the degradation time. Additionally, the osteogenic activity can be enhanced by the steady and predictable release of therapeutics (e.g., simvastatin) from the implanted composite, all without compromising the initial mechanical strength of the commonly used biomaterial CS.

The present invention provides for methods of using the bilayered composites. The methods comprise administering to the osseous tissue of a subject the bilayered composites as described herein. The subject can be a vertebrate animal, such as a bird, reptile, amphibian, fish or mammal. The subject may be a human. The osseous tissue may comprise bone or periodontal tissue. The bilayered composite may be applied directly to the tissue, such as through implantation during surgery or may be applied less invasively, such as through injection.

Once deposited, the bilayered composite remains in situ with the subject. As described herein, the bilayered composite may release one or more pharmaceutical agents within the subject. Further, as also described herein, the bilayered composite provides structural support to the tissue, as well as preventing or hindering surrounding soft tissue from migrating to the osseous tissue. As described herein, the degradable nature of both layers of the bilayered composite means that no additional surgery is required for removal, although it can be removed as needed.

EXAMPLES

Example 1

Bilayered Calcium Sulfate Composites
Metronidazole-Loaded PLGA Particles

Poly(lactic-co-glycolic acid) (Durect Corp., Birmingham, Ala.; 50:50; inherent viscosity: 0.55-0.75 dL/g; carboxylate end group) particles loaded with metronidazole (Sigma-Aldrich, St. Louis, Mo.) were created by film-casting and hand-grinding. Initially, 25 mg of metronidazole were combined with 200 mg of PLGA and dissolved in 1 mL of dimethyl sulfoxide (DMSO; an FDA Q3C Class 3 solvent). The solution was poured into a circular Teflon mold, frozen quickly at −80° C., and lyophilized to remove the DMSO. The dried film was hand ground to obtain particle sizes between 150-250 μm. A small amount of CS was used to prevent the polymer from sticking during grinding. The particles were washed with ethanol to remove residual CS powder on the surface of the polymer. Ethanol was chosen for washing to prevent drug loss because the low solubility of metronidazole in this solvent. Washed particles were vacuum-filtered, rapidly air-dried, and stored at −20° C. until used.

A short-term study of metronidazole-loaded microparticles was conducted to determine how much drug may be released during the setting phase of composite formation. For this purpose, 10 mg of washed PLGA particles were incubated at 37° C. in 1 mL of phosphate-buffered saline (PBS), pH 7.4. Supernatant was collected and replaced with fresh PBS every 15 min for the first hr, every 30 min for the 2$^{nd}$ hr, every hr for the 3$^{rd}$ and 4$^{th}$ hr, and finally increased to every 2 hr for the 6$^{th}$ and 8$^{th}$ hr time points. Supernatants were filtered (0.45 μm) and the absorbance measured at 318 nm.

Bilayered Calcium Sulfate Composites

Fabrication of the bilayered composites is illustrated in FIG. 1. The composites consisted of calcium sulfate hemihydrate (Sigma-Aldrich) as the structural matrix. First, blank CS samples without layers were produced by combining 1 g of CS with 800 μL of deionized (DI) water. The slurry was injected into a mold having a diameter of 6.3 mm and a height of 12.6 mm. The loaded mold was placed in a 43° C. oven for 24 hr to allow for the CS to completely set.

To begin formation of bilayered composites, cylindrical cores were produced in Teflon molds having a diameter of 4.7 mm and a height of 10 mm. A small, 8 mm long metal peg with a 0.63 mm diameter was fitted precisely in the center of the mold, with about 2.5 mm of the peg embedded into the core. The pegs suspended and centered the cores for shell production later. To make blank CS cores, 800 μL of DI water was added to 1 g of CS powder and mixed thoroughly in 3 mL non-sterile syringes fitted with a 16 gauge blunt needle. The slurry was loaded into the custom-fabricated Teflon mold and placed in a 43° C. oven for 24 hr to set the CS. For cores loaded with simvastatin, the same process was used, however 20 mg of simvastatin (Haouri Pharma-Chem, Inc., Edison, N.J.) were mixed along with the CS and DI water. Pegs were removed from the cores when they were dried, and the cores were stored at room temperature with desiccant until used.

To form the shell around the cores, another Teflon mold was created with cylindrical holes having the diameter of 6.3 mm and a height of 12.6 mm. The base plate was fabricated with 3.5 mm deep holes into which metal pegs were securely inserted. This depth allowed the cores to be positioned precisely in the center of the mold, thus allowing the shell to surround the core. Blank and simvastatin-loaded shells were created using the same method described above for the cores, where 1 g of CS was mixed with 800 µL of DI water, and in the case of simvastatin-loaded shells, 20 mg of drug were directly added. For samples containing metronidazole-loaded PLGA, the particles were added to both the blank and simvastatin-loaded shells at either 1 or 10 wt % and then mixed with 850 µL DI water in 3 mL syringes fitted with a blunt-tipped needle for easy, consistent filling of the mold. Using these formulations for the shells, bilayered composites were formed by filling the molds about half full. Next, prefabricated cores were quickly dipped in DI water to wet the surface, which allowed for smooth coverage of the shell slurry around the core, inserted into the mold, and pressed down onto the metal pegs until they stopped. The pegs positioned the cores and held them in place during setting of the shell slurry. The filled mold was placed into a 37° C. oven and allowed to dry overnight. For simplification, the different types of samples were given abbreviated names (Table 1).

TABLE 1

Abbreviations for the different sample types fabricated.
Codes are read: BSBC»(B)S(B)C»(Loading) in SHELL,
(Loading) in CORE.

| Shell Composition | Core Composition | Code |
| --- | --- | --- |
| Blank | Blank | BSBC |
| Blank | Simvastatin | BSSC |
| Simvastatin | Blank | SSBC |
| Simvastatin | Simvastatin | SSSC |
| 1 wt % PLGA | Blank | 1-BSBC |
| 1 wt % PLGA | Simvastatin | 1-BSSC |
| 1 wt % PLGA & Simvastatin | Blank | 1-SSBC |
| 1 wt % PLGA & Simvastatin | Simvastatin | 1-SSSC |
| 10 wt % PLGA | Blank | 10-BSBC |
| 10 wt % PLGA | Simvastatin | 10-BSSC |
| 10 wt % PLGA & Simvastatin | Blank | 10-SSBC |
| 10 wt % PLGA & Simvastatin | Simvastatin | 10-SSSC |
| No Layer Blank (No Drug) | | NL |

Note:
PLGA particles contained metronidazole.

The shells and cores described had a volume ratio of 50:50. Two other ratios were tested with simvastatin loaded into the shell only (SSBC), core only (BSSC), or both layers (SSSC). These samples were used to demonstrate how a change in the volume ratio would affect drug release from the composites. Table 2 lists the volume ratios used and the dimensions of the respective core and shell components. Custom molds were created to accommodate the different sizes, but the rest of the fabrication process was the same as described previously.

TABLE 2

Shell to core volume ratios and dimensions of
the bilayered composites

| Volume Ratio | Shell Height | Shell Diameter | Core Height | Core Diameter |
| --- | --- | --- | --- | --- |
| 50:50 | 12.6 mm | 6.3 mm | 10 mm | 4.7 mm |
| 70:30 | 9.6 mm | 4.7 mm | 6.2 mm | 3.2 mm |
| 85:15 | 9.6 mm | 4.7 mm | 6.2 mm | 2.4 mm |

Composite Microarchitecture
To monitor the distribution of PLGA particles within the CS shell matrix as well as the interface between shell and core, microcomputed tomography (microCT) was employed. Using a Scanco Medical µCT-40 scanner, specimens were evaluated at high resolution. Other parameters were set as follows: 156 µm increments, 0° angle, 70 kVp, 114 µA, 0.5 mm Al filter, and a voxel size of 8 µm. The raw images were qualitatively investigated for particle distribution trends, core orientation, and shell-core interaction. In addition, qualitative and quantitative assessment of the composites was conducted using a built-in 'bone trabecular morphometry' analytical tool with a lower threshold level of 130, gauss sigma of 3.0, and gauss support of 9. This script created a three-dimensional reconstruction that allowed visual assessment of cross-sections through the composite and provided the volume percentage of embedded polymeric particles and internal voids.

Composite Dissolution
Destructive testing was used to monitor dissolution of the bilayered composites. BSBC, 1-BSBC, and 10-BSBC samples were weighed, placed in separate 20 mL scintillation vials containing 12 mL of PBS and incubated on a plate shaker at 37° C. Every 4 d, replicate samples of each type were removed and dried at 43° C. overnight. For the remaining samples, the PBS was replaced with fresh solution. The dried samples were weighed to determine the amount of material remaining, which was then used to calculate the percentage of residual mass.

Mechanical Properties
Compression testing was performed to investigate any effects on mechanical properties caused by the layered geometry, simvastatin directly loaded into CS as well as the introduction of PLGA particles into the shell of the composites. All samples types listed in Table 1 were evaluated. Testing was accomplished using a Bose ELF 3300 system. Contact surfaces were lightly sanded, if necessary, to create parallel surfaces in contact with the compression platens. All samples were loaded at a rate of 0.5 N/sec until failure. Compressive modulus (M) and ultimate compressive strength (UCS) were calculated (Dowling N E. Mechanical behavior of materials: engineering methods for deformation, fracture, and fatigue. 2 ed. Upper Saddle River, N.J.: Prentice-Hall; 1999).

Drug Release from Bilayered Composites
Simvastatin Release
Release of simvastatin was measured for composites having shell to core volume ratios of 50:50, 70:30, and 85:15. BSBC, BSSC, SSBC, and SSSC samples for all volume ratios were prepared using the same simvastatin loading described in section 2.2. Samples were pre-weighed and submerged in PBS. Considering the overall size differences between the sample types, different volumes of PBS were used to maintain similar fluid volume to composite surface area ratios. To determine suitable sink conditions, the sample surface area to solution volume ratio of 50:50 samples was compared to those used in previous research (Oreliana B R, Thomas M V, Dziubla T D, Shah N M, Hilt J Z, Puleo D A. Bioerodible calcium sulfate/poly(β-amino ester) hydrogel composites. J Mech Behav Biomed. 2013; 26:43-53). A small pilot study showed that the dissolution rate of 50:50 samples remained constant for volumes above 10 mL (data not shown). To avoid saturation of CS or drug in PBS, a larger volume (12 mL) was used for the 50:50 samples. All other samples were placed in 4 mL, similar to previous release studies (Oreliana B R, Hilt J Z, Puleo D A. Drug release from calcium sulfate-based composites. J Biomed Mater Res B. 2014). To determine how simvastatin would be released from bilayered composites dissolving in non-sink conditions, 50:50 samples were also immersed in 8 mL of PBS. All samples were incubated at 37° C. on a plate shaker. Every 4 d, supernatant was collected and replenished with fresh PBS. Collected supernatant was treated with 100% ethanol in a 50:50 volume ratio to make sure all simvastatin was in solution. The mixture was then 0.45 urn-filtered and absorbance measured at 240 nm.

Multiple Drug Release

To investigate the kinetics of metronidazole and simvastatin release from bilayered CS composites, samples were pre-weighed, submerged in 12 mL of PBS, and incubated at 37° C. while on a plate shaker. Supernatant was collected and replenished every 4 d. Two aliquots from each sample were kept for measurement of metronidazole and simvastatin separately. Metronidazole in syringe-filtered (0.45 µm) supernatant was assayed directly using UV spectroscopy at 318 nm. Simvastatin was measured using high performance liquid chromatography (HPLC) on a Hitachi Primaide system fitted with a Kinetix C18 column (5 µm, 4.6×150 mm). Prior to measurement, supernatant was mixed with 5 mM EDTA (pH 8.0) at a 50:50 volume ratio and allowed to sit overnight. EDTA, a common chelating agent, was used to remove calcium ions that could precipitate during HPLC analysis. Next, this mixture was mixed with 100% ethanol in a 50:50 volume ratio to ensure complete dissolution of the poorly soluble simvastatin. The final sample composition was 25% supernatant, 25% EDTA, and 50% ethanol. A 70:30 (acetonitrile: DI water+0.01% trifluoroacetic acid) isocratic mobile phase at a flow rate of 1 mL per minute was used. Simvastatin was detected at 240 nm.

Statistics

Statistical analysis of the results was conducted using either a two-tailed unpaired t-test or one-way ANOVA. As appropriate, a Tukey-Kramer multiple comparison post hoc test was implemented. Linear regression was performed on sustained release profiles and the calculated slopes compared for significant differences using a two-tailed t-test. Differences between groups were considered to be significant with p-values <0.05.

Metronidazole-Loaded PLGA Particles

Figure 2:
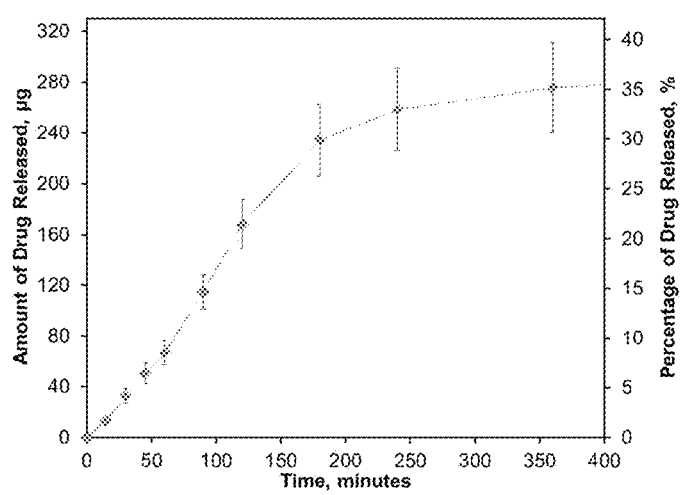
FIG. 2 shows cumulative release of metronidazole from 150-250 μm PLGA particles. Data are mean±standard deviation (n=3).

Metronidazole-loaded PLGA particles alone were first evaluated to determine how well the polymer controlled drug release. According to the results in FIG. 2, metronidazole was released steadily during the first 3 hr at a rate of about 4 µg per minute. Only about 8% of the drug was released during the first hr. After 3 hr, 30% of the total loading of metronidazole had been released. From this point forward, the release of drug from the particles slowed, with roughly 35% of the loaded metronidazole released after 6 hr.

Composite Microarchitecture

Qualitative Evaluation

Figure 3:
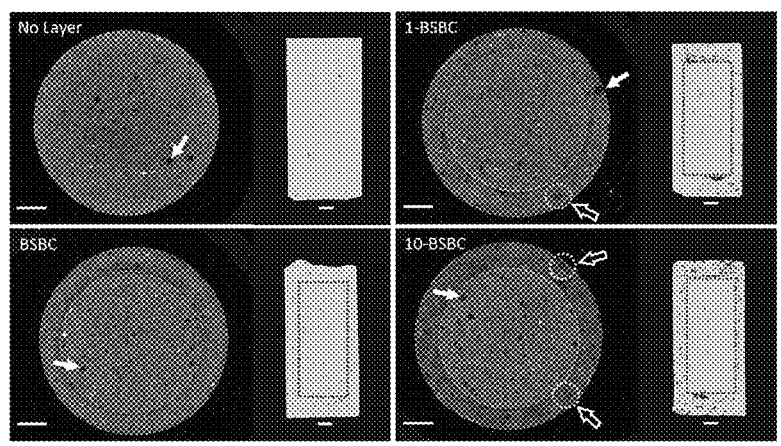
FIG. 3 shows representative microCT images of CS/PLGA composites: raw X-ray slices and cross-sections of 3D reconstructions. Closed arrows mark bubbles, and open arrows with circles indicate PLGA particles. Scale bars denote 1 mm.

MicroCT images showed the CS cores embedded within the layered composites and their interaction with the CS shells, as well as the distribution of PLGA particles embedded in the shells (FIG. 3). For comparison, results for a CS sample without layers (NL) are included. Minor defects (bubbles and other discontinuities) were found throughout the CS matrix in all samples. These defects were nearly spherical in nature and, thus, easily distinguishable from PLGA particles, which were irregularly shaped. The blank (drug-free) layered samples, BSBC, showed the CS core embedded within the CS shell and oriented parallel to the outer walls. The distribution of 1 wt % PLGA particles in the shells of 1-BSBC samples appeared to be homogeneous but sparse (FIG. 3, top right). In 10-BSBC samples with 10 wt % loading of particles in the shells, there was a homogeneous but more frequent distribution of particles throughout the CS shell (FIG. 3, bottom right). Similar to BSBC, both 1-BSBC and 10-BSBC had cores that were embedded in the center of the composite with a parallel orientation to the outer surface. Additionally, all layered samples had some minor defects located at the shell/core interface, with most of these discontinuities occurring near the top and bottom of the samples.

Quantitative Evaluation

Figure 4:
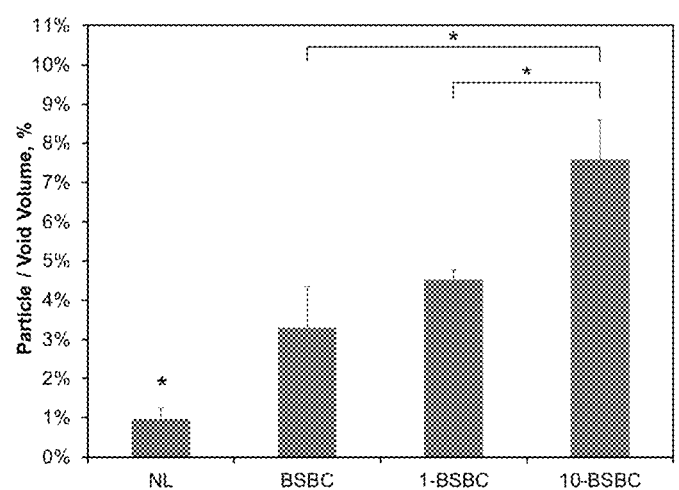
FIG. 4 shows volume percentage of voids/particles in CS/PLGA composites determined by microCT. Data are mean±standard deviation (n=5). Symbols (*) indicates significant differences (p<0.001).

Morphometric analysis was conducted to better assess the overall microarchitecture of bilayered CS samples. As shown in FIG. 4, the average volume percentage of voids in NL samples (0.96%) was significantly lower than that for all others (p<0.001). Furthermore, the particle content of 10-BSBC samples, 7.59%, was significantly higher (p<0.001) than that of both BSBC and 1-BSBC. Percentages for BSBC (3.30%) and 1-BSBC (4.52%) were not significantly different.

Composite Dissolution

Figure 5:
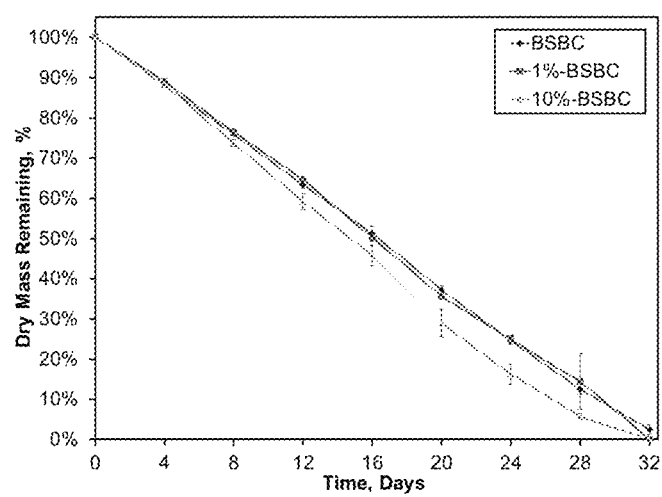
FIG. 5 shows mass loss profiles for bilayered blank CS and composites with 1 and 10 wt % PLGA loaded into the shells. Data are mean±standard deviation (n=3).

Loading 1 wt % of PLGA particles into the shells of bilayered composites did not have a significant effect on the dissolution rate (−3.1%/d) (FIG. 5). Increasing the loading to 10 wt % PLGA, however, significantly increased the dissolution rate to −3.43%/d (p<0.001), even though the time for complete dissolution differed by only about 4 d.

Mechanical Properties of Layered CS

Figure 6:
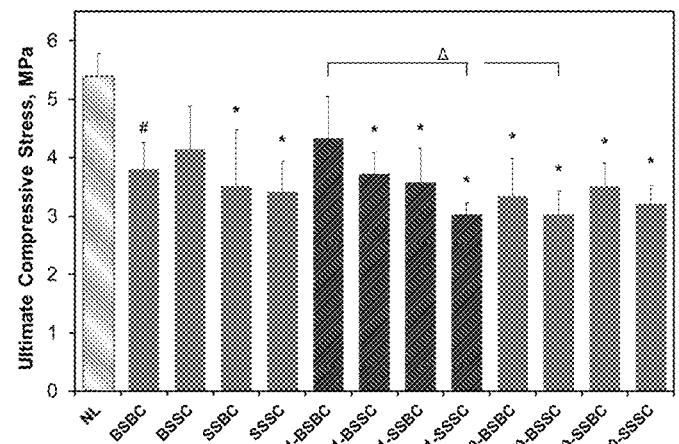
FIG. 6 shows mechanical properties of CS/PLGA composites with directly loaded simvastatin: A) ultimate compressive strength and B) compressive modulus. Data are mean±standard deviation (n=5). Symbols indicate significant differences: p<0.001 (*), p<0.01 (#), and p<0.05 (Δ).
Figure 6:
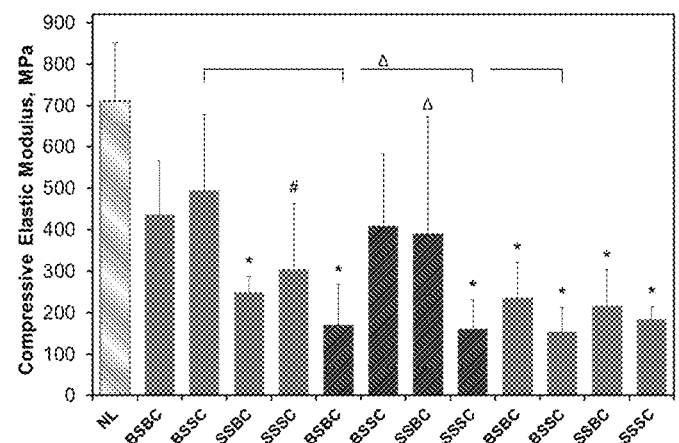

Fabrication of layered structures significantly affected the mechanical properties of CS composites (FIG. 6). The ultimate compressive strength of NL (5.40±0.38 MPa) samples was not significantly higher than that of BSSC (4.14±0.75 MPa) and 1-BSBC (4.33±0.72 MPa), but it was significantly greater than that for BSBC (3.80±0.46 MPa, p<0.01) and all other bilayered samples (p<0.001) (FIG. 6A). Within subgroups for PLGA particle loading, the strength of 1-BSBC (4.33±0.72 MPa) was significantly higher than that for both 1-SSSC (3.03±0.2 MPa) and 10-BSSC (3.03±0.4 MPa) (p<0.05). There were no other significant differences seen for layered samples, both loaded with PLGA and without.

The compressive elastic modulus of NL (712±139.6 MPa) was significantly higher (p<0.001) than that for SSBC (250±37.6 MPa), 1-BSBC (172±96.9 MPa), 1-SSSC (162±70.4 MPa), 10-BSBC (237±84.2 MPa), 10-BSSC (154±58.4 MPa), 10-SSBC (216±87.8 MPa), and 10-SSSC (184±29.6 MPa) bilayered samples (FIG. 6B). The average modulus of the blanks was also significantly greater than those of SSSC (306±157.6 MPa, p<0.01) and 1-SSBC (391±282 MPa, p<0.05). BSSC (495±184 MPa) samples had a significantly higher (p<0.05) modulus than did 1-BSBC (172±97 MPa), 1-SSSC (162±70 MPa), and 10-BSSC (154±58 MPa). There were no other significant differences between layered samples and their subgroups.

Drug Release from Bilayered Composites

Simvastatin Release

Figure 7:
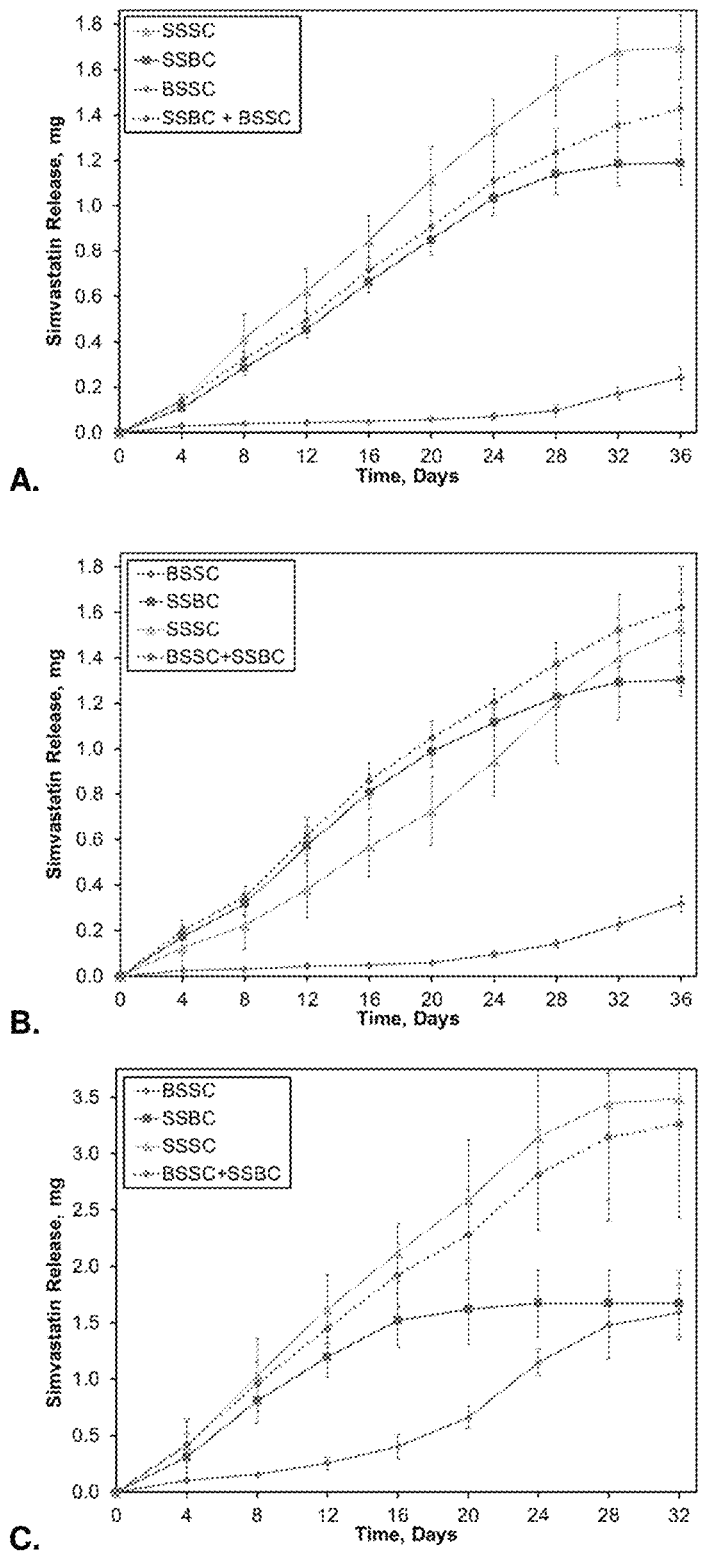
FIG. 7 shows cumulative release of simvastatin from bilayered samples having different shell to core volume ratios: (A) 85:15; (B) 75:25; and (C) 50:50. Data are mean±standard deviation (n=5).

To demonstrate temporally controlled release of simvastatin using bilayered composites, several experiments were conducted using different shell to core volume ratios. FIG. 7A shows the cumulative release of simvastatin from composites that had an 85:15 shell to core volume ratio. The sustained release of drug from samples with simvastatin loaded into both shell and core (SSSC), 0.055 mg/d, was significantly faster (p<0.001) than for SSBC (0.043 mg/d) and SSBC+BSSC (0.046 mg/d). Minimal drug loaded into the core only (BSSC) was released during the first 24 d. From that point until the samples dissolved, however, release of simvastatin from CS cores increased to 18 µg/d, whereas release from SSBC samples was finished. The total amount of simvastatin released from BSSC (shell) and SSBC (core) samples was 0.24±0.05 mg and 1.19±0.01 mg, respectively. The rate of release from BSSC was significantly slower than that for both SSSC (p<0.05) and SSBC+BSSC (p<0.01).

FIG. 7B shows the results for simvastatin released from composites consisting of 70% shell volume and 30% core volume. Over the first 20 d, the drug release rate from SSBC (0.046 mg/d) was significantly faster (p<0.01) compared to 0.041 mg/d for SSSC. Little to no drug was released from BSSC samples during the first 20 d, followed by an upward shift to a rate of 0.022 mg/d, which was significantly slower than the rates for both SSSC and SSBC+BSSC (p<0.01). For BSSC samples, 0.32±0.03 mg of drug was released. After 20 d of simvastatin release from SSBC samples, the shells had completely dissolved and released 1.30±0.07 mg of simvastatin.

The results for release of simvastatin from composites with a 50:50 shell to core volume ratio are depicted in FIG. 7C. For the first 16 d of the experiment, the rate of release from SSBC composites, 0.095 mg/d, was significantly slower (p<0.05) than that for SSSC (0.13 mg/d) and SSBC+BSSC (0.12 mg/d). During the same period, a small amount of drug was released from BSSC at a slow rate of 0.025 mg/d. After 16 d and until the composites dissolved, the rate of drug release from SSBC samples gradually slowed as the shell finished dissolving, a trend similar to what was observed in both FIGS. 7A and 7B. A total of 1.52±0.3 mg of drug was released from the shell. At its peak, the rate of release from BSSC samples, 0.10 mg/d, was not significantly different from the rates observed for SSSC and SSBC+BSSC samples, ultimately releasing a total 1.44±0.24 mg of simvastatin.

The total amount of simvastatin released from the cores (BSSC) for 50:50 (1.44±0.24 mg) samples was significantly different (p<0.001) than that for samples with either a 70:30 (0.32±0.03 mg) or 85:15 (0.24±0.05 mg) shell to core volume ratio. There was no significant difference in the total drug release between the 70:30 and 85:15 BSSC samples. For 50:50 SSBC samples, the total amount released (1.52±0.3 mg) from the shells was significantly different (p<0.001) than for 70:30 SSBC (1.30±0.07 mg) and 85:15 SSBC (1.19±0.1 mg) samples. In addition, the total amount of drug released from 70:30 SSBC samples was significantly different than from 85:15 SSBC samples (p<0.01). When comparing the total amount of drug released when SSBC and BSSC results are combined (SSBC+BSSC) to the total amount of drug released from SSSC samples, SSBC+BSSC specimens with an 85:15 shell to core volume ratio had a total combined release that was significantly lower (p<0.01) than the total amount of simvastatin released from the SSSC with the same volume ratio.

By reducing the volume of PBS from 12 mL to 8 mL, the dissolution time of samples having a 50:50 shell to core ratio was doubled (FIG. 8). During the first 32-36 d of incubation, simvastatin was released from both SSSC and SSBC samples at a rate of 0.074 mg/d and 0.077 mg/d, respectively. Also, a small amount of drug from BSSC samples was released during the same time frame at a rate of 0.009 mg/d. From day 36 until the end of the experiment (68 d), the rate for the SSSC samples continued steadily, however the rate of release from SSBC decreased to zero around 48 d. Additionally, the rate of release from BSSC samples increased to 0.051 mg/d and remained at this rate until the samples finished eroding.

Multiple Drug Release

Figure 9:
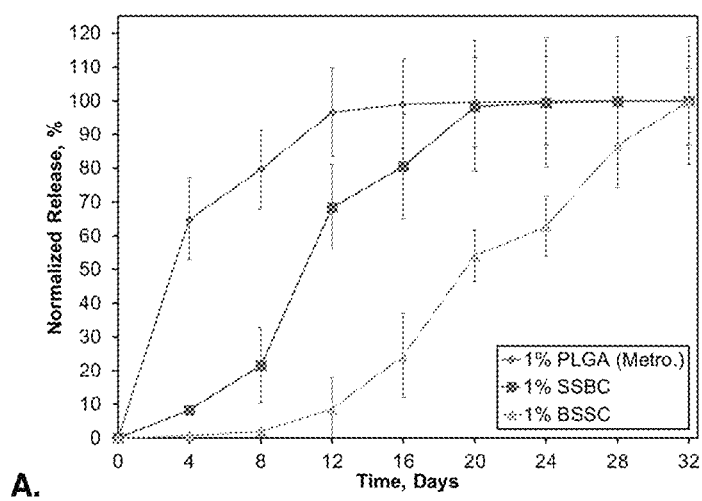
FIG. 9 shows cumulative release of simvastatin and metronidazole from bilayered composites. Normalized profiles of directly loaded simvastatin and metronidazole loaded into PLGA particles released from composites with (A) 1 wt % and (B) 10 wt % PLGA particles loaded in shells. Data are mean±standard deviation (n=5).
Figure 9:
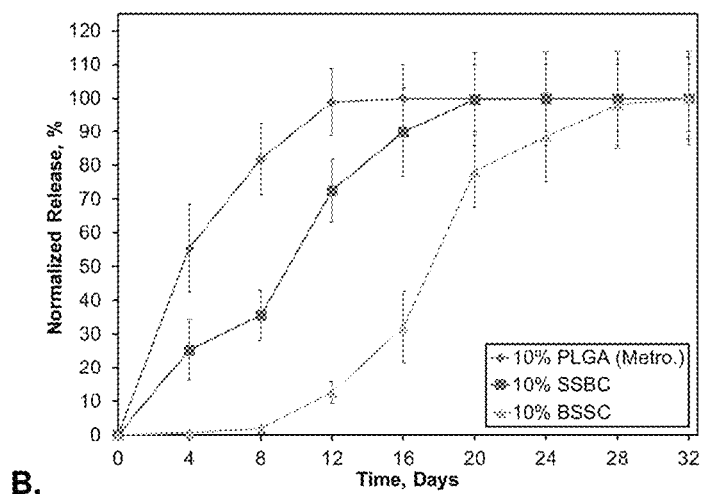

FIG. 9 shows results for release of metronidazole from PLGA particles embedded in CS shells as well as the release of simvastatin directly loaded in the shell or core of bilayered composites. The samples used for this experiment had a 50:50 shell to core volume ratio. Based on this ratio and the dissolution results presented in FIG. 5, the shell and core portions of the composites were predicted to dissolve completely in 14-16 d of the 28-32 d dissolution period for the complete composite. For composites with 1 wt % PLGA particles embedded in CS, a large amount of metronidazole (65%) was initially released from the shells during the first 4 d at a rate of 16.3%/d (FIG. 9A). After the initial burst of metronidazole, the release of drug slowed to a rate of 4.0%/d and continued to slowly decay to zero until the shells completely dissolved. Composites with 10 wt % PLGA particles showed a similar burst of metronidazole during the first 4 d, with as much as 55% of the total drug released (FIG. 9B). The rate of release of metronidazole decayed from 13.7%/d through the first 4 d, to 6.7%/d from days 4-8, and finally down to 0% by d 12 of the release. The results in FIG. 9 were normalized based on the amount of drug loaded into the respective layer rather than the complete composite. This allowed for direct comparison of the temporal release observed between metronidazole and simvastatin. When simvastatin was loaded into only the shell for 1 wt % and 10 wt % PLGA composites, metronidazole was initially released at a higher rate than simvastatin (2-6.3%/d). Because of the slow initial rate of simvastatin release, a short lag in the release profile developed, creating separation from the metronidazole profile and allowing for simvastatin to be released for up to 8 d longer. When the drugs were separated by keeping metronidazole-containing PLGA particles in the shell and loading simvastatin in only the core, 80-90% of the metronidazole was released over approximately 12 d before trace amounts of simvastatin were detected. After 16 d, the shells had completely dissolved, and metronidazole was no longer detected. In addition, the majority of simvastatin, isolated to only the core, was released starting after 12 d. Due to the layers separating the two drugs, a sequential release was observed with all metronidazole drug released prior to simvastatin.

Metronidazole-Loaded PLGA Particles

A previous study showed that loading a hydrophilic drug into carrier particles prior to embedding into a CS matrix significantly reduced the burst release witnessed when the drug was directly loaded into CS (Oreliana B R, Hilt J Z, Puleo D A. Drug release from calcium sulfate-based composites. J Biomed Mater Res B. 2014). Therefore, biodegradable PLGA microparticles were employed for the current study to assist with the sustained release of metronidazole from bilayered composites. Because the particles were exposed to water during the setting phase of CS, a release study was conducted using a larger volume of water than present during composite formulation to monitor the potential for premature release of drug from PLGA. No initial burst of drug was observed, indicating that the majority of the drug was contained within the PLGA microparticles during the formation of the composites.

Composite Microarchitecture

Qualitative assessment of the morphology of bilayered composites showed good distribution of PLGA microparticles embedded into CS shells at 1 and 10 wt %. The initial CS slurry was kept sufficiently fluid to prolong the working phase and allow for easy filling of the molds yet viscous enough to suspend PLGA particles during the setting phase. This trend has been shown in previous research in which hydrogel particles were uniformly distributed throughout a CS matrix using similar powder to liquid volume ratios (Oreliana B R, Thomas M V, Dziubla T D, Shah N M, Hilt J Z, Puleo D A. Bioerodible calcium sulfate/poly(β-amino ester) hydrogel composites. J Mech Behav Biomed. 2013; 26:43-53). Another study, showed the exposure of particles at or near the surface before dissolution followed the pitting of CS resulting from the release of particles from those locations after a short duration submerged in PBS (Oreliana B R, Hilt J Z, Puleo D A. Drug release from calcium sulfate-based composites. J Biomed Mater Res B. 2014). With the aid of small, metallic pegs, which were removed after fabrication, preformed blank and simvastatin-loaded cores were positioned in the center of the composites. Small defects were observed along the shell/core boundary. Many of these were air bubbles trapped as the CS set. Larger bubbles that appeared to accumulate near one end of the samples along the shell/core interface were most likely caused by an air pocket created when the cores were pressed into CS slurry.

Quantitative measurements assessed the particle volume fraction of bilayered CS composites. Although a significant increase in porosity was seen between samples containing 1 wt % and 10 wt % PLGA, the difference was not 10-fold. This lack of separation could be due to other defects, such as air pockets found along the shell/core interface. The script used to calculate the porosity is limited to only distinguishing between what is solid and what is not. The introduction of bubbles adds error to the calculations because these imperfections show up as radiolucent spaces similar to PLGA particles. Comparing the solid and layered samples demonstrates that defects strongly influenced on the porosity calculations.

Composite Dissolution

Calcium sulfate is a dense material that dissolves via surface erosion (Oreliana B R, Thomas M V, Dziubla T D, Shah N M, Hilt J Z, Puleo D A. Bioerodible calcium sulfate/poly(β-amino ester) hydrogel composites. J Mech Behav Biomed. 2013; 26:43-53; Thomas M V, Puleo D A. Calcium sulfate: properties and clinical applications. J Biomed Mater Res B. 2009; 886:597-610). Although the embedded PLGA particles were distributed throughout the CS matrix, they did not appear to be interconnected, which otherwise would have allowed for fluid to seep into the composite. During erosion, closed pockets with PLGA particles near the surface were exposed, releasing the polymer particles and increasing the surface area for further dissolution. Consequently, as the composites dissolved and PLGA particles were released, the surface area to volume ratio increased, allowing for faster dissolution of CS. Furthermore, because embedded PLGA particles did not change the dissolution characteristics of CS, the shorter lifespan when 10 wt % particles were added was related to the smaller overall volume of CS per sample that needed to dissolve. These trends have also been witnessed in a previous study in which dissolution of CS was observed after hydrogel particles were uniformly distributed throughout the composite (Oreliana B R, Thomas M V, Dziubla T D, Shah N M, Hilt J Z, Puleo D A. Bioerodible calcium sulfate/poly (β-amino ester) hydrogel composites. J Mech Behav Biomed. 2013; 26:43-53). Thus, the presence of polymer particles, even having different chemistries, affected only the duration of dissolution, depending on the amount of particles loaded, and not the nature of the dissolution process itself.

Mechanical Properties of Layered CS

To be a suitable alternative to autologous bone, the ideal synthetic material would have characteristics similar to those of tissue at the implantation site. CS has been described as having properties being similar to cancellous or trabecular bone (Hak D J. The Use of Osteoconductive Bone Graft Substitutes in Orthopaedic Trauma. J Am Acad Orthop Sur. 2007; 15:525-36). Investigating the mechanical properties of human trabecular bone from the mandible, Misch et al. measured an ultimate compressive strength of 3.9±2.7 MPa and elastic modulus of 96.2±40.6 MPa (Misch C E, Qu Z, Bidez M W. Mechanical properties of trabecular bone in the human mandible: Implications for dental implant treatment planning and surgical placement. J Oral Maxil Surg. 1999; 57:700-6). The introduction of a bilayered geometry significantly affected properties compared to solid CS samples, with up to a 44% and 78% reduction in the strength and elastic modulus, respectively. Note, however, that the properties of the layered composites were comparable to those of trabecular bone. The decrease in strength compared to the samples without layers could be due to the small air pockets along the shell/core interface acting as discontinuities within the composite, both at the interface parallel to the central axis of the cylinder as well as at the ends of the core. These stress concentrators contributed to a 17-44% decrease in the overall strength of the composites. The addition of either 1 or 10 wt % PLGA particles to CS shells did not have an effect when compared to blank bilayered samples. In previous research, as much as a 50-60% reduction in strength was seen following the addition of 10 wt % of gel particles to the monolithic CS matrix (Orellana B R, Thomas M V, Dziubla T D, Shah N M, Hilt J Z, Puleo D A. Bioerodible calcium sulfate/poly(β-amino ester) hydrogel composites. J Mech Behav Biomed. 2013; 26:43-53). In the present study, the PLGA particles were isolated to only the shell of the composites. Also, the presence of a solid blank core may have provided reinforcement for the composite, which may allow a greater range of PLGA particle loading that would provide greater control over the drug dose within the composites.

The loading of simvastatin directly into the shell, core, or both layers generally did not significantly affect the strength of the bilayered composites, even though isolated differences were observed (1-BSBC versus 1-SSSC and 10-BSSC). In another experiment conducted by Oreliana et al., loading of simvastatin directly into monolithic CS did not have a significant effect on the strength of the samples (Oreliana B R, Hilt J Z, Puleo D A. Drug release from calcium sulfate-based composites. J Biomed Mater Res B. 2014). Another group determined that up to 10% loading of simvastatin into calcium phosphate samples did not significantly affect the compressive strength (Yin H, Li Y G, Si M, Li J M. Simvastatin-loaded macroporous calcium phosphate cement: Preparation, in vitro characterization, and evaluation of in vivo performance. J Biomed Mater Res A. 2012; 100A:2991-3000). The present study had a lower loading of simvastatin (i.e., 2 wt %), however. Thus, direct loading of simvastatin does not affect the overall strength of different materials.

Drug Release from Bilayered Composites

The layered geometry used for the CS samples provided a unique platform for achieving a customizable sequential release of therapeutic agents. Loading of PLGA microparticles into the CS matrix allows for further tailoring of drug release.

Simvastatin Release

The present experiments were designed to demonstrate how the release of simvastatin can be tailored depending on which layer the drug was loaded in, whether it was the shell only, core only, or both. Furthermore, to illustrate the ability to adjust the duration or even the delay of drug release from either the shell or core, the shell to core volume ratio was altered. However, there were limitations to how much the volume ratio could be adjusted. For instance, the 50:50 shell to core ratio was considered the maximum. With the present dimensions, increasing the core volume beyond this point would create a thin and unstable shell. On the other hand, if the ratio was made so the shell would be greater than 85% of the total volume, the local concentration of drug released from the core could be too low to be therapeutically relevant.

For all of the release profiles that had simvastatin loaded in only the cores, there was a small amount of drug released from the start of composite dissolution up to when the core was completely exposed. Because the cores were suspended using a small metal peg that was later removed after the samples were fabricated, the hole that remained may have been large enough to allow a noticeable, but statistically insignificant, amount of simvastatin to be released.

In addition to investigating the effects of adjusting the shell to core volume ratio, the volume of PBS used for the release study was reduced from 12 mL to 8 mL. Because of the possible diverse environments in various implantation sites, it is likely for the implant to encounter different fluid volumes and/or turnover rates that may not allow for sink conditions. A small study demonstrated how release of simvastatin would change under non-sink conditions. To conduct the comparison, the 50:50 volume ratio was used. Interestingly, even with the reduction in the volume of PBS to 8 mL, the transition after shell depletion to core only erosion occurred around the halfway point, similar to the results seen under sink conditions. In previous work, the effects of fluid volume on the dissolution of CS were investigated (Orellana B R, Thomas M V, Dziubla T D, Shah N M, Hilt J Z, Puleo D A. Bioerodible calcium sulfate/poly (β-amino ester) hydrogel composites. J Mech Behav Biomed. 2013; 26:43-53). It was determined that the change in volume of fluid or even the turnover rate could have a large effect on the dissolution of CS (Orellana B R, Thomas M V, Dziubla T D, Shah N M, Hilt J Z, Puleo D A. Bioerodible calcium sulfate/poly(β-amino ester) hydrogel composites. J Mech Behav Biomed. 2013; 26:43-53). The duration of drug release can be greatly prolonged (doubled in the present study) using different fluid volumes. McLaren et al. also observed a large difference in the rate of drug release from calcium sulfate pellets when the fluid was completely refreshed at each time point versus exchanging only a fraction of the fluid volume (McLaren A C, McLaren S G, Nelson C L, Wassell D L, Olsen K M. The effect of sampling method on the elution of tobramycin from calcium sulfate. Clinical orthopaedics and related research. 2002:54-7). In the present study, although the rate of release slowed, the mechanism of drug release remained dependent on dissolution of CS. This could allow for tailoring of drug loading and/or the sample geometry according to the physiological conditions expected at the implant site.

Multiple Drug Release

A multiple drug release study was conducted to investigate the release kinetics of bilayered composites loaded with an antimicrobial agent and an osteogenic agent. Findings for samples with metronidazole in PLGA particles and simvastatin directly loaded into CS demonstrated sequential release. Polymeric particles loaded with metronidazole and embedded into the shell were exposed as CS experienced surface erosion, and sustained release of the drug occurred as the PLGA particles subsequently degraded. Release from both 1 and 10 wt % particles embedded into the CS shell was sustained until the shell portion of the bilayered composites completely dissolved. Controlled release of metronidazole from PLGA microspheres after an initial burst has been described as a possible treatment for periodontal disease (Tiwari G. Treatment Of Periodontal Diseases: Formulation consideration. Int J Pharm Bio Sci). By embedding particles into a CS matrix, the release of metronidazole was controlled throughout the first 16 d of the present study. In addition, previous research has demonstrated that drug-loaded hydrogel particles homogeneously distributed throughout a CS matrix allowed for a controlled release of drug, which only occurred due to the breakdown of particles exposed at the surface of the dissolving composite (Orellana B R, Thomas M V, Dziubla T D, Shah N M, Hilt J Z, Puleo D A. Bioerodible calcium sulfate/poly(β-amino ester) hydrogel composites. J Mech Behav Biomed. 2013; 26:43-53; Orellana B R, Hilt J Z, Puleo D A. Drug release from calcium sulfate-based composites. J Biomed Mater Res B. 2014).

With the intended use of these composites as a grafting substitute for alveolar bone augmentation, the oral cavity presents challenges for proper tissue regeneration due to the environment being rich with bacteria that can colonize natural and synthetic substrates. Thomas and Puleo described the implications of infection and inflammation in periodontal disease and tissue regeneration (Thomas M, Puleo D. Infection, Inflammation, and Bone Regeneration a Paradoxical Relationship. J Dent Res. 2011; 90:1052-61). Currently, the standard treatment for infected periodontal defects has antimicrobial agents being administered, either systemically or locally, prior to implantation of grafting material, which only delays the overall recovery of lost tissue (Nguyen A, Kim S, Maloney W, Wenke J, Yang Y. Effect of coadministration of vancomycin and BMP-2 on cocultured *Staphylococcus aureus* and W-20-17 mouse bone marrow stromal cells in vitro. Antimicrob Agents Ch. 2012; 56:3776-84; Lee F-Y, Chen D, Hu C-C, Hsieh Y-T, Liu S-J, Chan E-C. In Vitro and In Vivo Investigation of Drug-Eluting Implants for the Treatment of Periodontal Disease. AAPS PharmSciTech. 2011; 12:1110-5; Bernimoulin J P. Repeated local metronidazole-therapy as adjunct to scaling and root planing in maintenance patients. J Med Microbiol. 1999; 26:710-5). Administration of antimicrobial agents allows for better bone formation. Chen et al. investigated the effects of two different growth factors in a chronically infected bony defect in rat femurs (Chen X, Schmidt A H, Tsukayama D T, Bourgeault C A, Lew W D. Recombinant Human Osteogenic Protein-1 Induces Bone Formation in a Chronically Infected, Internally Stabilized Segmental Defect in the Rat Femur. J Bone Joint Surg. 2006; 88:1510-23). Although some healing occurred in the infected sites, the extent of bone formation was greater with the systemic administration of antibiotics (Chen X, Schmidt A H, Tsukayama D T, Bourgeault C A, Lew W D. Recombinant Human Osteogenic Protein-1 Induces Bone Formation in a Chronically Infected, Internally Stabilized Segmental Defect in the Rat Femur. J Bone Joint Surg. 2006; 88:1510-23). To further enhance the process of fighting infection and then regenerating lost tissue, release of an anti-bacterial agent from the graft starting at the time of implantation may prove beneficial to help reduce the overall healing time.

Many studies have investigated dual purpose implantable scaffolds, but none have employed a concentric cylindrical CS system as described in the present studies. Reis et al. developed drug-free, bilayered membranes comprising a continuous outer layer of PLGA with a porous calcium phosphate inner layer for the regeneration of lost periodontal tissue (Carlo Reis E C, Borges A P B, Araújo M V F, Mendes V C, Guan L, Davies J E. Periodontal regeneration using a bilayered PLGA/calcium phosphate construct. Biomaterials. 2011; 32:9244-53). For infected sites, Nguyen et al. developed a co-culture model using methicillin-sensitive *Staphylococcus aureus* and mouse bone marrow stromal cells to investigate the dual effects of an antibiotic, vancomycin, along with bone morphogenetic protein-2 (BMP-2) (Nguyen A, Kim S, Maloney W, Wenke J, Yang Y. Effect of coadministration of vancomycin and BMP-2 on cocultured *Staphylococcus aureus* and W-20-17 mouse bone marrow stromal cells in vitro. Antimicrob Agents Ch. 2012; 56:3776-84). Separately, the two agents were not effective, but when delivered together, the needed concentration of vancomycin was significantly reduced, suggesting that lower, non-toxic doses could be used (Nguyen A, Kim S, Maloney W, Wenke J, Yang Y. Effect of coadministration of vancomycin and BMP-2 on cocultured *Staphylococcus aureus* and W-20-17 mouse bone marrow stromal cells in vitro. Antimicrob Agents Ch. 2012; 56:3776-84). An in vivo study in which vancomycin and BMP-2 were delivered simultaneously from a biodegradable polyurethane scaffold demonstrated that bone formation could be regenerated within an infected defect (Guelcher S A, Brown K V, Li B, Guda T, Lee B H, Wenke J C. Dual-purpose bone grafts improve healing and reduce infection. J Orthop Trauma. 2011; 25:477-82). However, these systems release the drugs simultaneously. Considering the intent for the current device to help streamline the existing treatment process, it was encouraging to see metronidazole released before simvastatin, even when loaded into the shell together. The difference in the release kinetics can be explained primarily by the way the two drugs were loaded. Previous work has shown that release of drug from polymer particles embedded into a CS matrix had a rapid, initial burst followed by decay in the rate of release (Oreliana B R, Thomas M V, Dziubla T D, Shah N M, Hilt J Z, Puleo D A. Bioerodible calcium sulfate/poly(β-amino ester) hydrogel composites. J Mech Behav Biomed. 2013; 26:43-53; Oreliana B R, Hilt J Z, Puleo D A. Drug release from calcium sulfate-based composites. J Biomed Mater Res B. 2014). The lower rate is attributed to the decrease in surface area as CS degrades, leading to a smaller volume of particles exposed at the surface over time (Orellana B R, Thomas M V, Dziubla T D, Shah N M, Hilt J Z, Puleo D A. Bioerodible calcium sulfate/poly(β-amino ester) hydrogel composites. J Mech Behav Biomed. 2013; 26:43-53; Orellana B R, Hilt J Z, Puleo D A. Drug release from calcium sulfate-based composites. J Biomed Mater Res B. 2014). Simvastatin, on the other hand, is directly mixed with CS during sample formation, and due to the hydrophobic nature of the drug, it does not become segregated to the surface during the setting of CS. The release of simvastatin is, therefore, governed by the surface erosion characteristics of CS, which were shown to be linear. This allowed for a near constant rate of release of simvastatin. These differences in release kinetics between the two drugs and their means of loading allowed for enough separation for all the metronidazole to be released 4 d sooner than simvastatin. When simvastatin was loaded into only the core while PLGA particles loaded with metronidazole remained in the shell, there was a much greater lapse in time for a fully separated sequential release to occur, which may be useful for mimicking the clinical sequence of events for treating infection and subsequently restoring lost or damaged tissue.

In the present study, novel bilayered CS composites were investigated for their ability to provide tailored release of therapeutic agents as well as a sequential release of different drugs. Such a system may be useful as a bone graft substitute for treating infected bony defects, e.g., periodontal pockets. Although the shell and core geometry reduced mechanical strength of the composites, the properties were similar to those for mandibular trabecular bone. This may be an important trait that could allow for these implants to better mimic the surrounding target tissue being treated. Changing the shell to core volume ratio dictates the duration of drug release from each layer. When metronidazole and simvastatin were loaded together in the shell or in separate layers, temporal separation of the two drugs was achieved. Being able to tune such as system may help streamline the multiple steps needed to regenerate tissues more efficiently.

Example 2

Blank Samples

Figure 10:
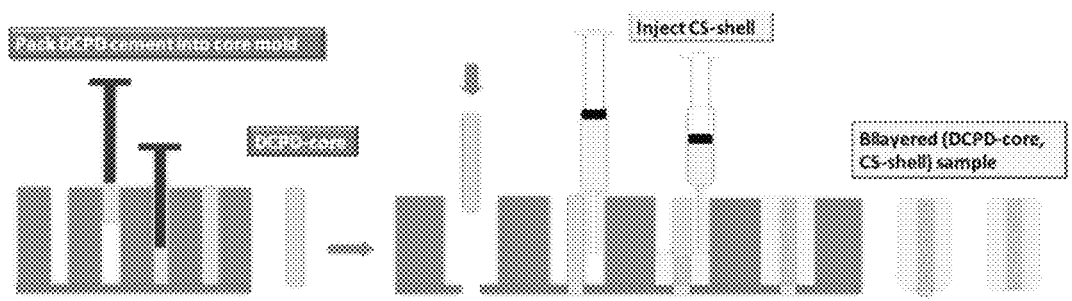
FIG. 10 shows a schematic depicting the packing of the DCPM core and injection of CS shell around the core. The bottom, red portion, of each mold is removable allowing for the punching out of the samples. Final adjustments are made to the exposed portion of the DCPM core by sanding it flush to the shell.

Bilayered calcium sulfate (CS) composites were produced according to FIGS. 1 and 10. CS slurries were prepared by mixing 1 gram CS powder with 800 µL of deionized water (DI). To create cores, prepared CS slurry was injected into a Teflon mold and kept at 43° C. for 24 hrs. Finished cores were suspended on a peg to center in a larger mold that allowed for a CS mixture to be injected, completely surrounding the CS core.

Drug Loaded Samples

To test the release of a bioactive agent from different CS layers, 20 mg (2 wt %) of simvastatin was directly mixed into 1 g of CS and combined with 800 µL DI and used to produce either the shell only loading (SSBC), core only loading (BSSC), or both shell and core loading (SSSC). For samples containing PLGA loaded with 12.5 wt % metronidazole, the particles were added to both the blank and simvastatin-loaded shells at either 1 or 10 wt % and then mixed with 850 µL DI water in 3 mL syringes fitted with a blunt-tipped needle for easy, consistent filling of the mold.

Bilayered Calcium Sulfate/Calcium Phosphate Composites

To enhance mechanical stability, dicalcium phosphate dihydrate (DCPD) was added to the bilayered implants (FIG. 10b). CP slurries were prepared by combining 1 g DCPD (a mixture of monocalcium phosphate monohydrate and β-tricalcium phosphate with a 1:1 molar ratio) powder and 400 µL of 100 mM sodium citrate. Cores with either CS or DCPD slurries were packed into a mold and kept in either a 43° C. oven or a desiccator under vacuum for 24 hr, respectively. Finished cores were inserted in a larger mold that allowed for a slurry mixture to be packed around the cores. Final samples consisted of CP blanks, CP-shell/CS-core, and CS-shell/CP-core.

The process illustrated in FIG. 10 depends on a variety of parameters, including but not limited to:

Slurry mixture for calcium sulfate composites is fluid enough to be injected allowing for consistent easy filling of the molds.

To suspend the calcium sulfate cores small metallic pegs were inserted allowing for accurate and consistent orientation. Pegs were removed before testing.

For calcium sulfate/calcium phosphate implants, prefabricated DCPD cores were correctly oriented in the mold for shell production via a small insert located on the bottom plate of the mold.

DCPD was packed under pressure into the molds.

Although the compressive properties decreased with the introduction of a layered geometry, the resulting strengths for calcium sulfate bilayered composites remained either similar to or stronger than the strength of trabecular bone in the mandible. Calcium sulfate/calcium phosphate samples were even stronger still. Further, preformed scaffolds can be designed to allow fabrication of a variety of shapes.

Figure 11:
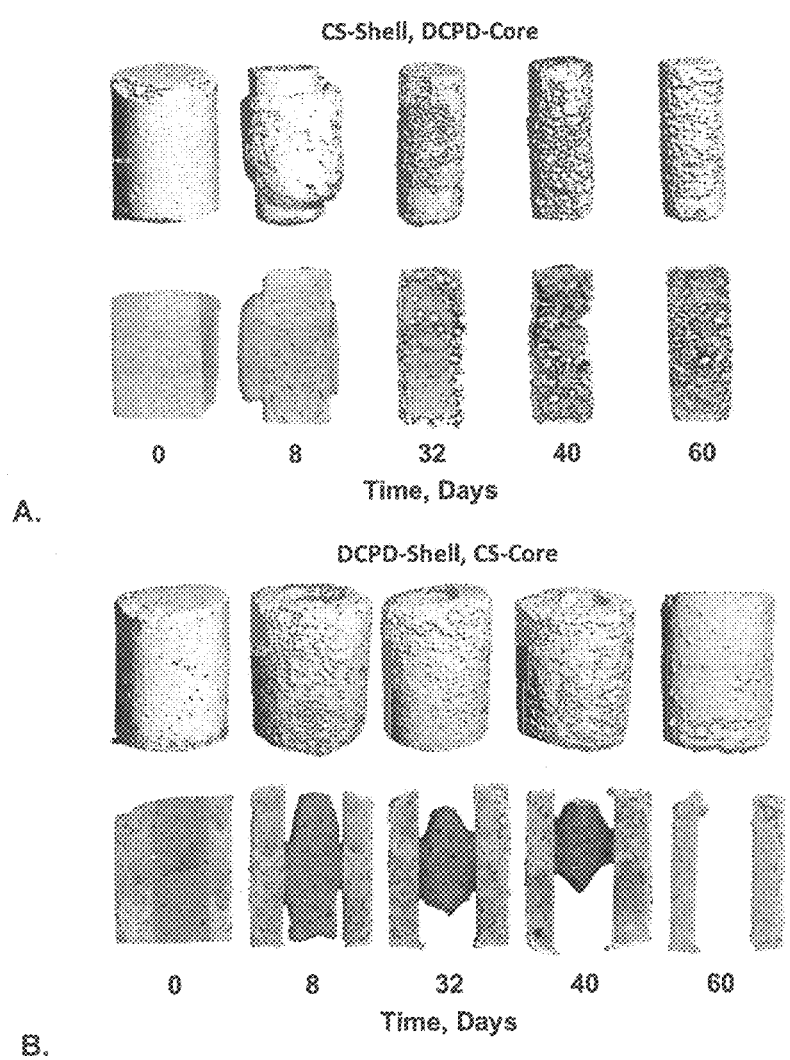
FIG. 11 shows microCT reconstructions of microarchitectural changes for A.) CS in shell, DCPD in Core samples, and B.) DCPD in Shell, CS in Core samples.
Figure 18:
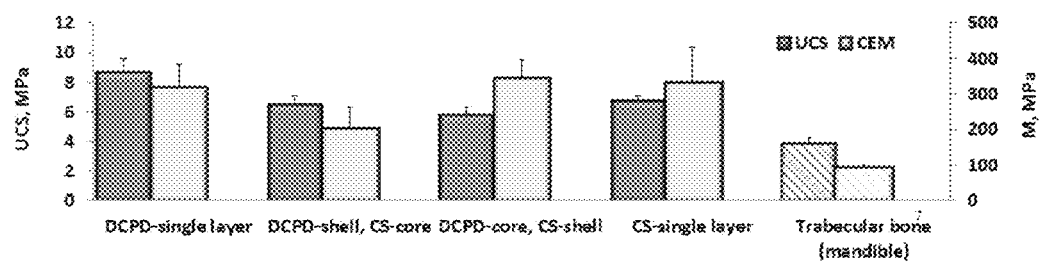
FIG. 18 shows compression testing results displaying the ultimate compressive stress (UCS, left) and the compressive elastic modulus (M, right).

Mechanical testing was measured using a Bose ELF 3300 system and demonstrated the ultimate compressive strength (UCS) and compressive elastic modulus (M) of the materials (FIG. 18). These data demonstrate the effect of the bilayered geometry compared to the single layer samples and trabecular bone. Further, microcomputed Tomography (microCT) demonstrated the structural integrity of the layered components and allowed for analysis of structural changes during the erosion of the bilayered materials (FIG. 11).

Figure 19:
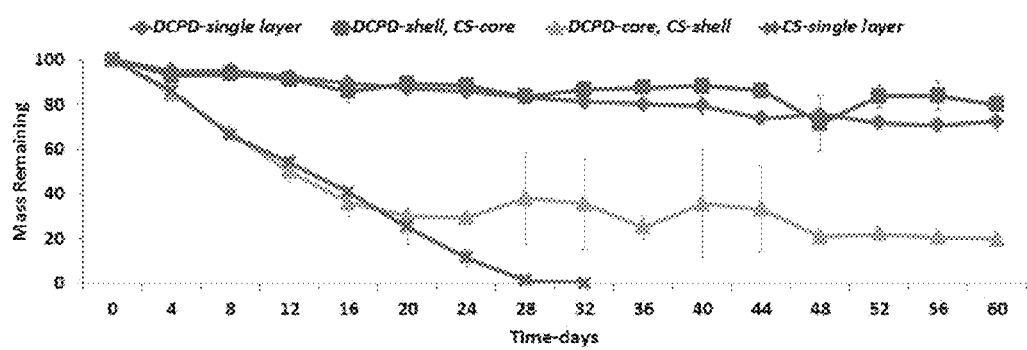
FIG. 19 shows representative mass loss (top) and pH (bottom) during destructive degradation testing.

Tests were also performed on the destructive degradation of the bilayered composites. These data allowed for the evaluation of the erosion process of the samples. Samples were weighed and placed in separate plastic vials containing 4 mL of PBS, and all the samples were incubated on a shaker plate at 37° C. Every 4 days replicate samples were collected and dried at 43° C. for a minimum of 24 hours. Dried samples were weighed to determine mass loss. FIG. 19 shows representative data for mass loss and pH. The erosion pattern of the layered materials has potential for erosion tuning and customizable drug release that could be useful for a bone graft substitute.

Example 3

Drug-Loaded Bilayered Calcium Sulfate/Calcium Phosphate Composites

CS slurries were prepared by mixing 1 gram calcium sulfate hemihydrate (Sigma-Aldrich) with 800 µL of deionized (DI) water. To test the release of a bioactive agent, 10 mg (1 wt %) of simvastatin was directly mixed into the CS prior to addition of water. CS blanks were also made without the addition of simvastatin The CS slurry was then injected into a cylindrical Teflon mold of average height 6.5 mm and diameter 4.75 mm and then kept at 43° C. for 24 hrs. Any trapped air was removed by tapping the mold on a hard surface as the slurry sets. CS samples were then removed and stored in a dry environment at room temperature. CS samples had an average dry weight of 0.10±0.02 g.

Adapting from what was originally proposed by Lemaitre et al. (Lemaitre, J.; Mirtchi, A. A.; Mortier, A. Calcium phosphate cements for medical use: State of the art and perspectives of development. *Silic. Ind.* 1987, 9-10, 141-146), DCPD slurries were prepared by combining a mixture of MCPM and β-TCP with a 1:1 molar ratio at 1 gram total mass with 400 µL of 100 mM sodium citrate as a setting retardant to form the DCPD. Similar to CS, simvastatin was added to the 1 gram powder mixture prior to mixing with citrate at 10, 20 and 50 mg (1 wt %, 2 wt %, and 4.8 wt %, respectively). Mixing the components after the addition of sodium citrate—rather than prior—helps to slow the setting of the mixture. The DCPD slurry was packed firmly into a cylindrical Teflon mold of height 6.5 mm and diameter 4.75 mm. Any trapped air was removed by tapping the mold on a hard surface as the slurry sets. The samples were then allowed to set in a fume hood at room temperature for 24 hrs. DCPD samples were then removed and stored in a dry environment at room temperature. DCPD samples had an average dry weight of 0.17±0.008 g.

In order to prepare CS-shell-DCPD-core (CS/CP) samples, DCPD slurry was prepared. The slurry can also be mixed with 2 wt % simvastatin for a drug loaded core (CPs). The slurry was then packed into a cylindrical Teflon mold of height 10 mm and diameter 2.35 mm. The cement was then allowed to set in a fume hood at room temperature for 24 hrs. The samples were then removed and held in place at the center of a wider Teflon mold of height 6.5 mm and diameter 4.75 mm. The samples were held in place using thin molds of equivalent diameter. CS slurries were then prepared with some as blanks and some with 1 wt % of simvastatin to form a simvastatin loaded CS shell (CSs). The slurries were then injected around the DCPD samples and any trapped air was removed tapping the mold on a hard surface as the slurry sets. The samples were kept in a dry environment at 42° C. as they set. The resulting bilayered samples were carefully removed from their mold and any DCPD extruding from the CS was sanded down. Samples were then removed and stored in a dry environment at room temperature.

For the preparation of DCPD-shell-CS-core (CP/CS) samples, DCPD slurries were prepared with and without the addition of 2 wt % simvastatin. The slurry is then packed into a cylindrical Teflon mold of height 6.5 mm and diameter 4.75 mm with a 10 mm height and 2.35 mm diameter steel dowel rod held in place in the center with a thin mold of equivalent diameter. After being packed, the cement was allowed to set in a fume hood at room temperature for 24 hrs. The dowel rods were then punched out carefully without significantly damaging the DCPD shell. CS slurries were then prepared with and without the addition of 1 wt % simvastatin. The slurries were then injected at the center of the DCPD shell. Any trapped air was removed by tapping the mold on a hard surface as the slurry sets. The samples were kept in a dry environment at 42° C. as they set. The resulting bilayered samples were carefully removed from their mold. Samples were then removed and stored in a dry environment at room temperature.

Simvastatin Release Study

Release studies were conducted on DCPD samples at simvastatin loadings of 1, 2, or 4.8 wt % (CP-1, CP-2, and CP-4.8, respectively). The same was done for CS samples but only at 1 wt % (CS-1). Blanks of CS and DCPD were made for comparisons. Studies on release of bilayered CP/CS and CS/CP samples were conducted with drug loadings and layering of CS/CPs, CPs/CS, CPs/CSs and CSs/CPs. DCPD layers were 2 wt % and CS layers with 1 wt %. All release studies were performed using 4 mL phosphate-buffered saline (PBS), pH 7.4, at 37° C. and on a plate shaker. At the end of every 4 days, samples were transferred into new vials with 4 mL of PBS and the supernatant from the previous vials were analyzed using UV spectroscopy. Release supernatant was mixed with an equal volume of reagent alcohol to dissolve any remaining simvastatin. After filtering at 0.45 µm, absorbance was measured at 240 nm.

Compressive Mechanical Testing

Bilayered and non-layered CS and DCPD samples were mechanically tested in compression using a BOSE ELF 3300 system. After measuring dimensions, samples were loaded to failure at a rate of 0.5 N/s. From each sample's stress-strain curve, compressive elastic modulus [$E_c$] and ultimate compressive stress [$\sigma_{ult}$] were calculated.

Destructive Degradation Testing

A total of 30 unloaded non-layered DCPD samples were weighed and each sample was immersed in 4 mL of PBS. These samples were then allowed to dissolve at 37° C. on a plate shaker. The supernatant was aspirated and the samples were refilled with PBS at the end of every 4 days. At the end of every 8 days, 3 samples were collected, allowed to dry, and then weighed for percent change in mass.

Microcomputed tomography (microCT) was used to evaluate the internal structure of samples during erosion. Samples were analyzed with a Scanco Medical µCT-40 scanner. The specimens were evaluated with standard resolution having 250 projections with 1024 samples each.

Additional parameters were set as follows: 92 μm increments, 01 angle, 70 kVp, 114 μA, 0.5 mm Al filter, and a voxel size of 12 μm. The resulting images were used to construct a three dimensional model with a built-in 'bone trabecular morphology' analytical tool at a lower threshold of 109. The scans and 3D image were then assessed qualitatively for obvious changes in the internal structure.

Statistics

Statistical analysis of the results was performed using either a two-tailed, unpaired t-test or one-way ANOVA. As appropriate, this was followed with a Tukey-Kramer multiple comparisons post hoc test. Any outliers were determined using Grubbs' test. Differences between groups were considered to be significant with p-value <0.05.

Simvastatin Release Study

Figure 12:
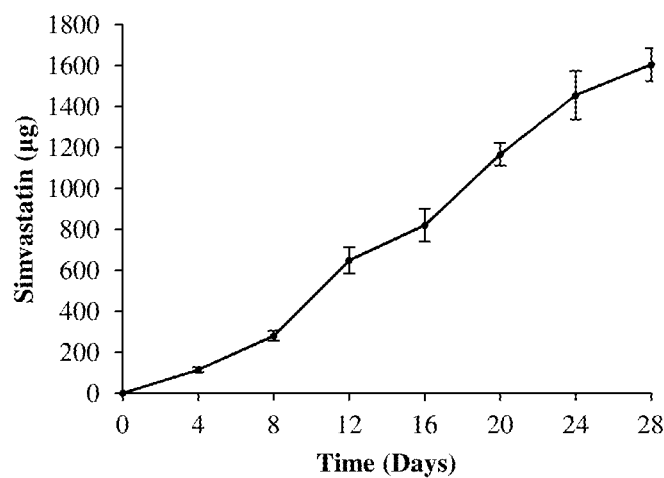
FIG. 12 shows cumulative release of simvastatin from CS (top) and DCPD (bottom) samples at 1 wt % Data is mean±standard error of mean (SEM) (n=5).
Figure 12:
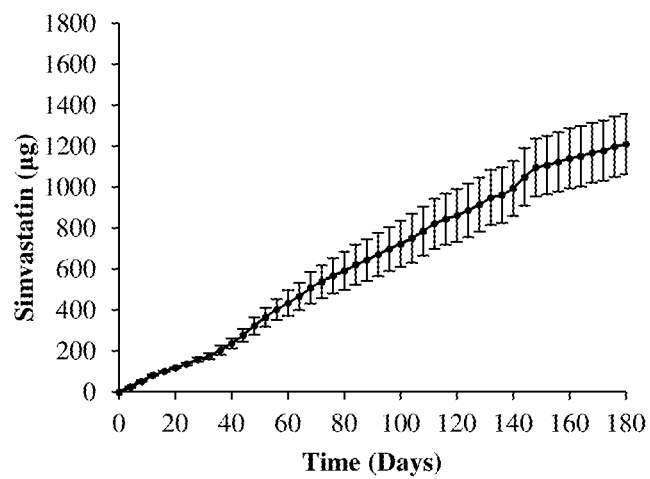

Release of simvastatin from CS samples occurred at a much higher rate than DCPD samples, as expected from CS's faster dissolution rate. Within 28 days, CS samples were fully dissolved through surface erosion. FIG. 12 shows release profiles for CS and DCPD samples loaded each with 1 wt % simvastatin (CS-1 and CP-1). Release rates were approximately 247 and 29 μg/day for CS-1 and CP-1, respectively. Increasing the amount of simvastatin added to DCPD resulted in a loading-dependent increase in release rate (i.e., 45 and 105 μg/day for 2 and 4.8 wt % simvastatin loadings, respectively).

Figure 13:
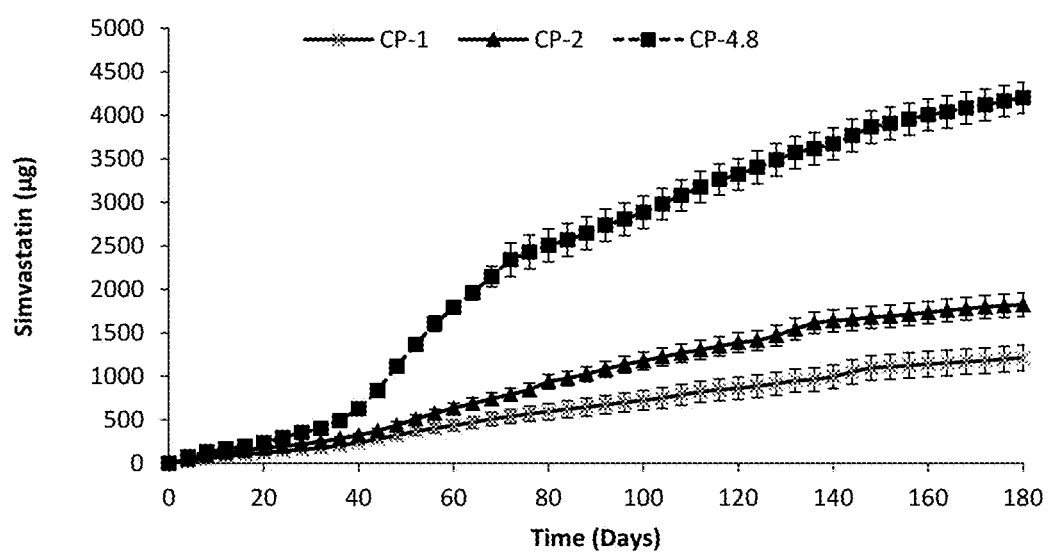
FIG. 13 shows cumulative releases of simvastatin from DCPD samples at 1 wt %, 2 wt %, and 4.8 wt %. Data is mean±SEM (n=5).

FIG. 13 shows the release profiles for CP-1, CP-2 and CP-4.8 and indicates a less linear cumulative release at higher loadings. This is especially visible in CP-4.8 release profile where a large increase in release rate was seen between 32 and 76 days. During the first 32 days of release the rate for CP with 10, 20 and 4.8 wt % simvastatin was 22, 29, 47 μg/day, respectively. From days 32 to 72, the release rate for the three samples increased to 37, 57, and 206 μg/day, respectively. After the 72 days, the release rate for the three samples dropped to 26, 39, and 72 μg/day, respectively. At the end of the 180 study of DCPD release, CP-1, CP-2, and CP-4.8 released a cumulative amount of 1.21±0.33 mg, 1.82±0.30 mg, and 4.20±0.40 mg, respectively,—all of which are significantly different from each other ($p<0.05$). Interestingly, CP-2 released a similar amount in the 180 days compared to the total release of CS (1.82±0.30 mg and 1.60±0.18 mg, respectively).

Figure 14:
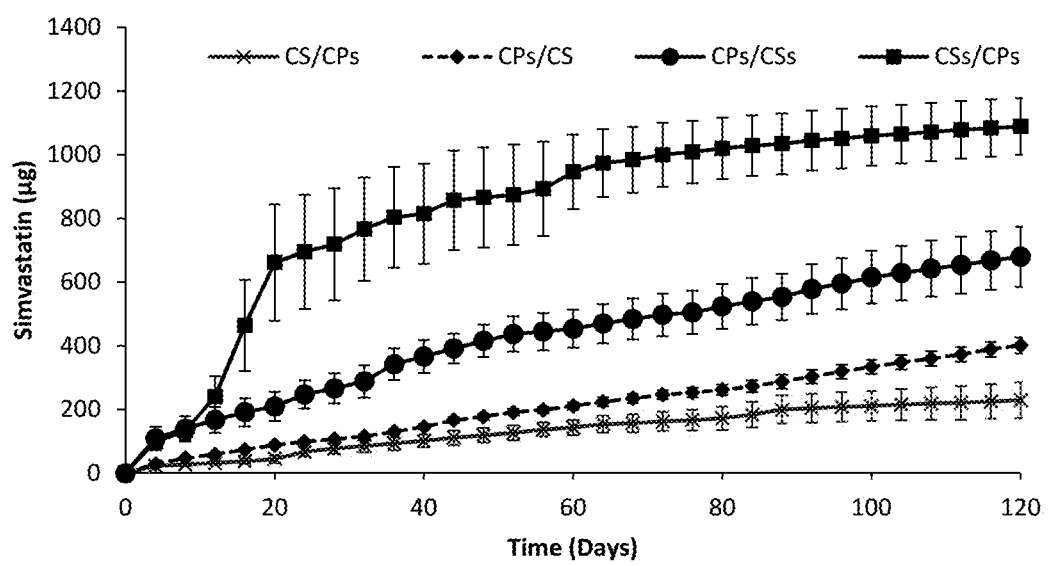
FIG. 14 shows cumulative releases of simvastatin from CSs/CPs, CPs/CSs, CPs/CS, and CS/CPs. Simvastatin loadings are denoted by the lowercase s. 2 wt % is loaded in DCPD layers and 1 wt % in CS layer.

At the end of the 120 day period, CS/CPs, CPs/CS, CPs/CSs, and CSs/CPs released a cumulative amount of 229±57 μg, 401±125 μg, 679±210, 1169±197 μg, respectively (FIG. 14). Compared to the cumulative release of CP-1, CP-2, and CP-4.8 samples at 120 days (862±288 μg, 1388±255 μg, 3319±402 μg), CSs/CPs and CPs/CSs had a cumulative release comparable ($p>0.05$) to CP-2 and CP-1, respectively. Bilayered DCPD and CS samples released simvastatin at much slower rates compared to their non-layered counterparts at almost all instances. CSs/CPs experienced the greatest average release rate of 7.5 μg/day. However, the release was not steady ($R^2=0.755$); CSs/CPs had an average release of 32 μg/day in the first 20 days which then decreasing to 4.1 μg/day from then on. All other loadings experienced a much more steady release. CPs/CSs, CPs/CS, and CS/CPs released simvastatin at an average of 5 μg/day, 3.1 μg/day, and 1.92 μg/day, respectively.

It is important to note that after conducting Grubb's test for outliers, it was found that CP-1 and CP-4.8 each had one sample with more than 10 timepoints that were considered outliers; nevertheless, these outliers remain represented in FIG. 14. With a sample size of 5 and confidence interval of 95%, G=1.672. A total of 45 data points were collected yet one CP-1 sample released significantly higher on 33 timepoints ($G>1.672$). One CP-4.8 sample also released significantly higher on 28 data points ($G>1.672$). Outliers in release were observed in other samples and categories however they did not occur as significantly frequent as the ones mentioned previously. No outliers were found in bilayered release samples Compressive Mechanical Testing Mechanical testing showed DCPD to all have significantly ($p<0.05$) greater ultimate compressive strength and compressive modulus than did CS (FIG. 15). There were no significant differences ($p>0.05$) in the two properties between DCPD blanks and the simvastatin loaded DCPD samples tested. The same quality was observed when comparing blank CS and simvastatin loaded CS.

Additionally the strength and modulus of both bilayered samples were significantly lower ($p<0.01$) than those of DCPD blanks. Interestingly, the compressive mechanical properties of both bilayered samples were comparable ($p>0.05$) to that of CS blanks. There was also no significant difference found between the compressive mechanical properties of CS/CP bilayering compared to CP/CS bilayering (modulus—219±140 MPa and 220±68 MPa, respectively; strength—4.6±1.7 and 6.7±1.6, respectively).

It is important to note that three outliers in modulus were found and removed from CS-1, CP-1 and CS/CP using Grubb's test for outliers. Data of one sample was missing for both CS-1 and CP-1, resulting in a sample size of 9. At a sample size of 10 and 9 with a confidence interval of 95%, G=2.176 and 2.11, respectively. It was found that a sample in CS-1 and CP-1 each had a significantly higher modulus ($G>2.11$) compared to its 8 other samples and was removed accordingly from the data as modulus sample size was adjusted to 8 for CS-1 and CP-1. One sample in CS/CP was found to be significantly higher as well for modulus and was removed according from the data as modulus sample size was adjusted to 9 for CS/CP.

Destructive Degradation Study

Figure 16:
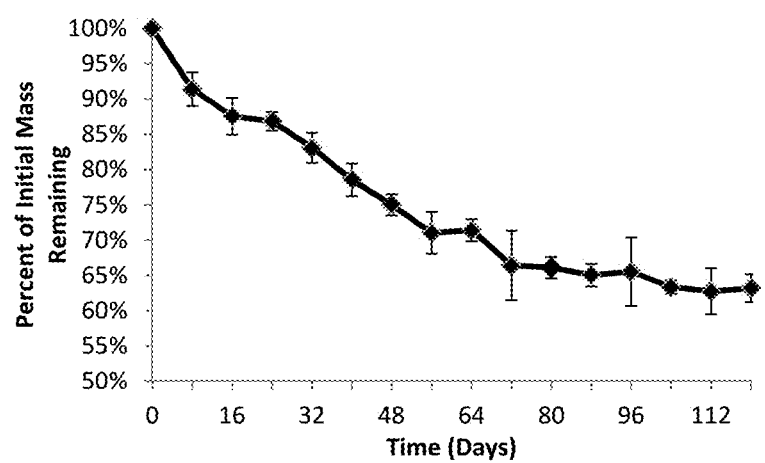
FIG. 16 shows percentage of initial mass remaining from DCPD samples at every 8 days over a period of 128 days. Data are mean±SEM (n=3).

Over a period of 128 days, data was collected on the percent of remaining mass in samples every 8 days. The data showed a fairly constant decrease in mass (FIG. 15); however the change in percent remaining mass decreased gradually as the study progressed, suggesting a more logarithmic relationship. Percent loss in mass was fairly consistent between samples, indicated by the standard deviation bars. Between any two consecutive time points, there was no significant difference in mass loss ($p>0.05$), however at the end of the 120 days there accumulated a significant ($p<0.001$) mass loss of 36.8±2%. MicroCT scans also showed qualitatively that DCPD developed a porous internal structure as it eroded (FIG. 16).

Simvastatin Release Study

As loadings increased in non-layered DCPD samples, a larger release rate was seen between 32 and 76 days. The increase was much less obvious in lower loadings, however it can be clearly seen in 50 wt % loadings. It was observed that the average daily release suddenly increased in all DCPD samples between 32 and 76 days before decreasing to a rate slightly higher than the initial release rate during the first 32 days. The sudden increase can be due to the formation of porous structures within the sample which increase surface area within the sample and proportionally increase simvastatin release. The subsequent drop in release can be attributed to the partial transformation of DCPD to the less soluble calcium deficient hydroxyapatite (CDHA) (~0.088 g/L vs. ~0.0094 g/L at 25° C., respectively) (Dorozhkin S V, Calcium Orthophosphates in Nature, Biology and Medicine. *Materials.* 2009; 2(2):399-498) which precipitated over time within and as a layer around the sample, thereby slowing the release of drug.

In a similar in vitro study on the compositional changes during degradation in β-TCP and MCPM formulations of DCPD, there were slight CDHA conversions observed in a period of 14 days (Alge, D. L., Goebel, W. S., Chu, T-M. G. (2013) Effects of DCPD cement chemistry on degradation properties and cytocompatibility: comparison of MCPM/β-TCP and MCPM/HA formulations. *Biomedical Materials*, 8.2, 1-8). Acknowledging that conversions from DCPD to CDHA require crystal nucleation as the rate-limiting step (Bohner M et al 2003 Compositional changes of a dicalcium phosphate dihydrate cement after implantation in sheep. *Biomaterials* 24 3463-74), it is likely that slight initial CDHA conversions provided for nucleation sites for further CDHA precipitation. Based on observation and results, the precipitation of CDHA may have occurred both within DCPD as it dissolved to form its porous matrix and outside as a layer around the sample. As complex porous structures formed within the DCPD sample, it became increasingly more difficult for dissolved calcium and phosphate ions to leave the sample, leaving a saturated environment within the DCPD. This in turn would force the precipitation of the ions as the more stable and less soluble CDHA. The same effect may have occurred outside the sample due to higher concentrations of calcium and phosphate ions around the sample due to dissolution at the surface and slight precipitation. This effect can be seen in the mass loss of non-layered DCPD samples which slows over a 120 day period despite increasing surface area due to increasing porosity. Thus, there is evidence to suggest a conversion of DCPD into CDHA which works to slow dissolution and drug release.

The results from the release study suggest that higher loadings should be preferred over lower loadings in order to have a higher average release rate, while lower loadings are preferred over higher loadings in order to have a steadier release rate. Of the three loadings tested, CP-2 seems to be the ideal candidate for a higher release rate while maintaining its steadiness of release. Studies have shown beneficial effects of 1.2 mg topical application in human trials of simvastatin for mandibular defects (Pradeep A R, Priyanka N, Kalra N, Naik S B, Singh S P, Martande S. Clinical efficacy of subgingivally delivered 1.2-mg simvastatin in the treatment of individuals with Class II furcation defects: a randomized controlled clinical trial. J Periodontol. 2012; 83:1472-9; Pradeep A R, Thorat M S. Clinical effect of subgingivally delivered simvastatin in the treatment of patients with chronic periodontitis: a randomized clinical trial. J Periodontol. 2010; 81:214-22; Rao N S, Pradeep A R, Bajaj P, Kumari M, Naik S B. Simvastatin local drug delivery in smokers with chronic periodontitis: a randomized controlled clinical trial. Aust Dent J. 2013; 58:156-62).

Knowing the performance of non-layered CS-1 and non-layered CP-2, behavior of bilayered release of simvastatin with CS and DCPD layers can be predicted to an extent. Due to CS's rapid dissolution, CSs-shell layering was predicted to have a higher release rate in the first 28 days of its dissolution. This was supported by the release profile of CSs/CPs in this experiment whose release in the first 20 days was 780% greater than its release rate after that point. Additionally, CS-shell samples would result in greater mass loss since more surface area is exposed to outside conditions, leaving behind the slower degrading DCPD core. This is beneficial for providing longer-lasting scaffolding for implantations while also allowing room for sufficient bone growth as the outer CS layer dissolves.

While CS dissolves much more rapidly than DCPD, its degradation can be retarded by surrounding it with the DCPD shell. In all CS core samples, CS dissolution lasted longer than the 28 days for CS non-layered samples and there was not as dramatic of an initial release as that of CSs/DCPDs samples. This quality is especially important for improved biocompatibility since the early dissolution of CS in CS/CP samples is associated with a significant drop in pH levels (McQuinn, M. (2014, September). *Bilayered Calcium Phosphate/Calcium Sulfate Bone Graft Substitutes*. Poster presented at the 96$^{th}$ Annual Scientific Sessions & Exhibition, Honolulu, Hi.). The release of simvastatin from DCPDs/CSs samples was much steadier than CSs/DCPDs.

As expected, DCPDs/CS and CS/DCPDs formulations had a slower yet more linear release rate compared to other bilayered formulations. DCPDs shells release at a higher rate by occupying more volume compared to DCPDs cores. The formation of an empty core as DCPD-shell samples dissolve can also be beneficial for providing greater mechanical strength than a DCPD core while also allowing for bone growth to occur at the center of the shell. This can also help to promote the resorption of precipitated CDHA by increasing surface area.

It is important to note that the release of simvastatin is less predictable due to the effect of precipitation of CDHA as DCPD dissolves (Xie, J., Riley, C., Chittur, K. Effect of albumin on brushite transformation to hydroxyapatite. *J. Biomed. Mater. Res.* 2001, 57, 357-365; Ginebra, M. P.; Canal, C.; Espanol, M.; Pastorino, D.; Montufar, E. B. Calcium phosphate cements as drug delivery materials. *Adv. Drug Deliv. Rev.* 2012, 64, 1090-1110). Additionally, there is evidence to show that hydroxyapatite may form from CS formulations as well (Nilsson, M., Wang, J-S., Wielanek, L., Tanner, K. E., Lindgren, L. (2004). Biodegradation and biocompatibility of a calcium sulfate-hydroxyapatite bone substitute. *The Journal of Bone & Joint Surgery (Br)*, 86-B, 120-125). The formation of the apatite layer results in slowed release and was observed in this experiment. In two of the CSs/DCPDs formulations, portions of the CSs outer layers developed a hard shell that prevented them from fully dissolving the expected 28 days. This was also observed in DCPDs/CSs formulations where the dissolution of CSs was halted by the precipitation of CDHA on both ends of the cylinder.

Compressive Mechanical Testing

Blank DCPD samples tested in this study had an overall mean compressive strength that was 219% higher than that of the blank CS samples (14.27±2.46 MPa vs. 6.52±1.04 MPa). However, there were no significant changes (p>0.05) found in strength and modulus as loadings increased in CS and DCPD compared to their respective blanks. The quality for DCPD and CS to retain its mechanical properties at the loadings tested in this experiment allows for more options in controlled drug release which is important for regions of bone defect where healing is slower and requires increased drug loadings to compensate.

It is important to note that DCPD samples have mechanical properties much greater than their CS counterparts and this is seen in FIG. 14. Consequently, the addition of DCPD to CS in a bilayered formation was expected to effectively enhance the modulus and strength. However, properties were similar to those of non-layered CS. Regardless, the mechanical properties observed in this experiment were comparable to or exceeded those of trabecular bone in the mandible (96.2 MPa modulus; 3.9 MPa strength) (Misch C E, Qu Z, Bidez M W. Mechanical properties of trabecular bone in the human mandible: Implications for dental implant treatment planning and surgical placement. *J Oral Maxil Surg.* 1999; 57:700-6; McQuinn, M. (2014, September). *Bilayered Calcium Phosphate/Calcium Sulfate Bone Graft Substitutes.* Poster presented at the 96th Annual Scientific Sessions & Exhibition, Honolulu, Hi.). Furthermore, a redeeming quality in bilayered samples is that the inclusion of DCPD allows for an adequate support structure in implantation sites much longer than CS samples due to its slower dissolution. Additionally, as discussed in the previous section, simvastatin loaded DCPD/CS layering allow for a steady and long term release.

Destructive Degradation Study

The DCPD biocements formulated in this experiment possess beneficial degradation properties for the purposes of promoting bone augmentation. DCPD forms porous structures as it degrades through bulk degradation. These non-erodible matrices form as DCPD degrades due to continuous dissolution and precipitation which result in less soluble CDHA crystals precipitating from the β-TCP, MCPM, and sodium citrate mixture (Bohner, M. pH variations of a solution after injecting brushite cements. *Key Eng. Mater.* 2001, 192-195, 813-816; Alge, D. L., Goebel, W. S., Chu, T-M. G. (2013) Effects of DCPD cement chemistry on degradation properties and cytocompatibility: comparison of MCPM/β-TCP and MCPM/HA formulations. *Biomedical Materials,* 8.2, 1-8. http://stacks.iop.org/1748-605X/8/i=2/a=025010). Contrastingly, CS undergoes surface erosion as it dissolves. The structure of DCPD as it degrades can allow for infiltration of mesenchymal cells while osteogenic activities are promoted by the local release of simvastatin. MicroCT scans showed slight surface imperfections in DCPD samples even before degradation testing began. These surface imperfections were found to be as wide as 100 µm in diameter which is sufficient for infiltration of osteoblasts (20-30 µm). A study done by Zerbo et al (2005) confirmed the possibility of cell infiltration in porous β-TCP samples through connected micropores as samples underwent dissolution (Zerbo, I. R., Brockers, A. L. J. J., Lange, G., Burger, E. H. (2005) Localization of osteogenic and osteoclastic cells in porous β-tricalcium phosphate particles used for human maxillary sinus floor elevation. *Biomaterials,* 26.12, 1445-1451).

Another property of the 13-TCP/MCPM formulation of DCPD is its ability to maintain pH as it degrades compared to other formulations such as MCPM and hydroxyapatite which significantly lower pH levels (Alge, D. L., Goebel, W. S., Chu, T-M. G. (2013) Effects of DCPD cement chemistry on degradation properties and cytocompatibility: comparison of MCPM/β-TCP and MCPM/HA formulations. *Biomedical Materials,* 8.2, 1-8). This is an important factor to sustain biocompatibility of the samples.

A problem with CS is its rapid dissolution which has been shown in animal trials and can have unfavorable outcomes (Thomas, M. V., Puleo, D. A., Calcium sulfate: A review. *J. Long Term Eff. Med. Implants,* 15(69):599-607, 2005, 29(5):282-288, 2001; Nilsson, M., Wang, J-S., Wielanek, L., Tanner, K. E., Lindgren, L. (2004). Biodegradation and biocompatibility of a calcium sulfate-hydroxyapatite bone substitute. *The Journal of Bone & Joint Surgery* (Br), 86-B, 120-125). This is presumably due to the rapid loss of CS mass and loss in mechanical properties which may not provide sufficient time or conditions for bone augmentation to occur. DCPD's much slower degradation rate may remedy this issue. In this study, over a period of 120 days, DCPD samples maintained 63.18±2% of their initial mass while CS dissolved in 28 days. The much slower degradation rate in DCPD observed is also beneficial for maintaining a slow consistent release over a sustained period time as observed in the release study.

For the purposes of effectively promoting bone growth while maintaining a strong support structure, simvastatin loaded CP/CS bilayered bioceramics may be an effective alternative to CS for procedures such as GBR. While CS proves to be a highly biocompatible and biodegradable material, its rapid dissolution is a quality that is largely undesired for larger areas of defect where bone healing would take longer than the 28 days which CS permits. The rapid dissolution of CS leads to the decline in its mechanical properties and can also generate gaps where bone growth 'lags' behind (Nilsson, M., Wang, J-S., Wielanek, L., Tanner, K. E., Lindgren, L. (2004). Biodegradation and biocompatibility of a calcium sulfate-hydroxyapatite bone substitute. *The Journal of Bone & Joint Surgery* (Br), 86-B, 120-125). Additionally, non-layered DCPD may not be ideal either due to its much slower degradation rate (>180 days) which will permit little bone growth as the sample degrades. These issues can be addressed by combining the two ceramics using CP/CS bilayered bioceramics by providing a longer lasting support structure (DCPD) while also permitting sufficient bone growth to occur within the core as the faster degrading CS is dissolved. After bone ingrowth has occurred within the core of the DCPD shell, mechanical properties can expect to see a boost due to the presence of both bone and DCPD. Additionally, cell infiltration and resorption can occur on both sides of the DCPD shell, thereby allowing for better integration of bone and effectively reducing the degradation time of DCPD. Additionally, the osteogenic activity will be enhanced by the steady and predictable release of simvastatin from the sample, all without compromising the initial mechanical strength of the commonly used CS.

CS and DCPD are both proven alternatives to conventional bone grafts. DCPD possesses advantages such as stronger mechanical strength, prolonged release, and internal conditions which promote bone growth. Preferred loading amounts in DCPD were determined to be 2 wt %, and increased loadings up to 4.8 wt % did not affect the mechanical strength of the material. Additionally, bilayered CS and DCPD samples were tested where it was discovered that CSs/CPs samples released more simvastatin at any period of its degradation compared with any other layering option, however CSs/CPs had a much steadier release rate and higher mechanical strength which is equivalent to that of CS. Bilayered CS and DCPD samples may allow for more options for treatment of bone defects rather than using solely CS or DCPD. Ultimately, the use of one bioceramic over the other will depend on the desired compressive strength, degradation, and drug release when confronted with different sites for bone augmentation. However, CPs/CSs formulations seem to be a more interesting candidate for future in vivo testing and applications.

The foregoing descriptions of various embodiments provide illustration of the inventive concepts. The descriptions are not intended to be exhaustive or to limit the disclosed invention to the precise form disclosed. Modifications or variations are also possible in light of the above teachings. The embodiments described above were chosen to provide the best application to thereby enable one of ordinary skill in the art to utilize the inventions in various embodiments and with various modifications as are suited to the particular use contemplated. All such modifications and variations are within the scope of the invention. All publications, patents and patent applications referenced herein are to be each individually considered to be incorporated by reference in their entirety.

We claim:

1. A bilayered bone graft composite for bone augmentation comprising an outer shell layer comprised of a first bioceramic and an inner core layer comprised of a second bioceramic, wherein the first and second bioceramics are different such that one layer degrades in situ within a subject at a rate faster than the other layer to allow for cell infiltration in situ with the slower degrading layer preformed to mechanically support the bilayered bone graft composite and surrounding tissue in situ and further wherein the inner core layer is encased by the outer core layer.

2. The bilayered composite of claim 1, wherein the outer shell layer degrades faster than the inner core layer.

3. The bilayered composite of claim 1, wherein the inner core layer degrades faster than the outer shell layer.

4. The bilayered composite of claim 1, wherein one layer comprises a material selected from the group consisting of dicalcium phosphate dihydrate (DCPD), hydroxyapatite, calcium-deficient hydroxyapatite, carbonate-substituted hydroxyapatite, and calcium polyphosphate.

5. The bilayered composite of claim 4, wherein the other layer comprises a material selected from the group consisting of calcium sulfate (CS), β-tricalcium phosphate, amorphous calcium phosphate, monetite, and tetracalcium phosphate.

6. The bilayered composite of claim 1, wherein one layer comprises calcium sulfate and the other layer comprises calcium phosphate.

7. The bilayered composite of claim 6, wherein the calcium phosphate is dicalcium phosphate dihydrate.

8. The bilayered composite of claim 1, wherein at least one layer further comprises a pharmaceutical agent selected from the group consisting of: simvastatin, lovastatin, rosuvastatin, bone morphogenetic proteins, human parathyroid hormone fragment 1-34, metronidazole, doxycycline, vancomycin, gentamycin, ciprofloxacin, ketoprofen, celecoxib, diclofenac, meloxicam or combinations thereof.

9. The bilayered composite of claim 8, wherein both layers further comprise a pharmaceutical agent.

10. The bilayered composite of claim 8, wherein the pharmaceutical agent is preloaded in a degradable matrix or a hydrogel.

11. The bilayered composite of claim 1, wherein the subject is an animal.

12. The bilayered composite of claim 1, wherein the subject is a human.

13. The bilayered composite of claim 1, wherein the outer layer further comprises polymer particles.

14. The bilayered composite of claim 1, wherein the inner layer further comprises polymer particles.

15. The bilayered composite of claim 1, wherein the inner layer and the outer layer form concentric cylinders.

16. A method of providing tissue support to a subject in need thereof, comprising administering the bilayered composite of claim 1 to tissue of the subject.

17. The method of claim 16, further comprising preloading one layer with a pharmaceutical agent.

18. The method of claim 17, wherein the pharmaceutical agent is in a degradable matrix or hydrogel within the layer.

19. The method of claim 16, wherein both layers further comprise preloading with a pharmaceutical agent.

20. The method of claim 16, wherein the tissue is osseous tissue.

* * * * *